(12) United States Patent
Cohen et al.

(10) Patent No.: US 12,053,501 B2
(45) Date of Patent: *Aug. 6, 2024

(54) METHODS FOR TREATING SYMPTOMS OF DRY EYE DISEASE

(71) Applicants: Tufts Medical Center, Boston, MA (US); Trustees of Tufts College, Medford, MA (US); On Target Therapeutics LLC, Wellesley, MA (US)

(72) Inventors: Charles Cohen, Weston, MA (US); Krishna Kumar, Cambridge, MA (US); Alan S. Kopin, Wellesley, MA (US); Benjamin N. Harwood, Boston, MA (US); Venkata S. Raman, Medford, MA (US); Pedram Hamrah, Wellesley, MA (US)

(73) Assignees: Tufts Medical Center, Boston, MA (US); Trustees of Tufts College, Medford, MA (US); On Target Therapeutics LLC, Wellesley, MA (US)

( * ) Notice: Subject to any disclaimer, the term of this patent is extended or adjusted under 35 U.S.C. 154(b) by 171 days.

This patent is subject to a terminal disclaimer.

(21) Appl. No.: 17/521,366

(22) Filed: Nov. 8, 2021

(65) Prior Publication Data

US 2022/0054581 A1     Feb. 24, 2022

Related U.S. Application Data

(63) Continuation of application No. 16/070,467, filed as application No. PCT/US2017/014605 on Jan. 23, 2017, now Pat. No. 11,197,906.

(60) Provisional application No. 62/286,070, filed on Jan. 22, 2016.

(51) Int. Cl.
| | |
|---|---|
| *A61K 38/08* | (2019.01) |
| *A61K 9/00* | (2006.01) |
| *A61K 38/00* | (2006.01) |
| *A61K 47/54* | (2017.01) |
| *A61K 47/60* | (2017.01) |
| *A61K 47/65* | (2017.01) |
| *A61P 27/02* | (2006.01) |
| *A61P 29/00* | (2006.01) |

(52) U.S. Cl.
CPC ........... *A61K 38/08* (2013.01); *A61K 9/0048* (2013.01); *A61K 38/00* (2013.01); *A61K 47/543* (2017.08); *A61P 27/02* (2018.01); *A61P 29/00* (2018.01); *A61K 47/60* (2017.08); *A61K 47/65* (2017.08)

(58) Field of Classification Search
CPC ...... A61K 38/08; A61K 9/0048; A61K 38/00; A61K 47/543; A61K 47/60; A61K 47/65; A61P 27/02; A61P 29/00
See application file for complete search history.

(56) References Cited

U.S. PATENT DOCUMENTS

| | | | |
|---|---|---|---|
| 5,200,473 | A | 4/1993 | Jeanneret-Gris |
| 5,284,656 | A | 2/1994 | Platz et al. |
| 5,451,569 | A | 9/1995 | Wong |
| 6,416,738 | B1 | 7/2002 | Theodore |
| 7,169,892 | B2 | 1/2007 | Atsushi et al. |
| 9,545,452 | B2 | 1/2017 | Wang et al. |
| 10,233,219 | B2 | 3/2019 | Cohen et al. |
| 11,197,906 | B2 | 12/2021 | Cohen et al. |
| 11,254,720 | B2 | 2/2022 | Cohen et al. |
| 2002/0086020 | A1 | 7/2002 | Lee |
| 2004/0197314 | A1 | 10/2004 | Delcarye |
| 2006/0263336 | A1 | 11/2006 | Caplan |
| 2008/0020942 | A1 | 1/2008 | Raines |
| 2009/0238808 | A1 | 9/2009 | Drewes |
| 2010/0260681 | A1 | 10/2010 | Brennan |
| 2012/0172235 | A1 | 7/2012 | Winter |
| 2012/0245229 | A1 | 9/2012 | Ji et al. |
| 2013/0004592 | A1 | 1/2013 | Wu |
| 2014/0349943 | A1 | 11/2014 | Gadek |
| 2019/0135882 | A1 | 5/2019 | Cohen et al. |
| 2022/0135633 | A1 | 5/2022 | Cohen et al. |

FOREIGN PATENT DOCUMENTS

| | | |
|---|---|---|
| JP | 2010/229093 | 10/2010 |
| JP | 2019507182 A | 3/2019 |
| WO | WO 2005/121755 A1 | 12/2005 |
| WO | WO 2014/168721 A2 | 10/2014 |

OTHER PUBLICATIONS

Doyle et al., JBC 289(19):13385-13396, May 9, 2014 (Year: 2014).*
Cash et al., Drug Discovery Today, vol. 19, No. 8, pp. 1186-1192 Aug. 2014 (Year: 2014).*
clinicaltrials.gov record for Study NCT00799552 (Year: 2010).*
Ambizas and Patel, US Pharm. 2010;35(4):34-41 (copy provided 12 pages). (Year: 2010).*
Fortin et al., (2009) Proc. Natl. Acad. Sci. U.S.A. 106, 8049-8054 (Year: 2009).*
Harwood et al., (2013) Mol. Pharmacol. 83, 814-821 (Year: 2013).*
Fahim et al., BMC Ophthalmology 2006, 6:20, 7 pages (Year: 2006).*

(Continued)

*Primary Examiner* — Melissa L Fisher
*Assistant Examiner* — Joseph Fischer
(74) *Attorney, Agent, or Firm* — COOLEY LLP; Matthew Pavao; J. Nancy Costigliola

(57) ABSTRACT

The present disclosure relates to, among other things, compositions and methods for treating an inflammatory condition including, but not limited to, ocular inflammation, dry eye disease, and ocular neuropathic pain. One aspect of the present disclosure relates to a composition comprising (a) chemerin or a fragment or analog thereof and (b) a lipid entity linked to the chemerin or fragment or analog thereof.

8 Claims, 17 Drawing Sheets

Specification includes a Sequence Listing.

(56) References Cited

OTHER PUBLICATIONS

Shimamuru, Peptides 30 (2009) 1529-1538 (Year: 2009).*
Adjei et al., "Pulmonary Delivery of Peptide Drugs: Effect of Particle Size on Bioavailability of Leuprolide Acetate in Healthy Male Volunteers", Pharm Res, 1990, vol. 7, p. 565-569.
Al-Fulaij et al., Pharmacological analysis of human D1 and D2 dopamine receptor missense variants, J. Mol. Neurosci, 2008, vol. 34, p. 211-223.
Ambizas et al. "Treatment Options for Dry Eye Disease", US Pharmacist, 2010, vol. 35, No. 4, p. 34-41.
Bennett and Xie, "A peripheral mononeuropathy in rat that produces disorders of pain sensation like those seen in man", Pain, 1988, vol. 33, p. 87-107.
Bentley, R. "Chirality in Biology", Encyclopedia of Molecular Cell Biology and Molecular Medicine, 2nd Edition, 2004, p. 579-618.
Best, "Click Chemistry and Bioorthogonal Reactions: Unprecedented Selectivity in the Labeling of Biological Molecules", Biochemistry 2009, vol. 48, p. 6571-6584.
Beutler, B. "Innate Immunity: an overview", Molecular Immunology, 2004, vol. 40, p. 845-859.
Braquet et al., "Effect of Endothelin-1 on Blood Pressure and Bronchopulmonary System of the Guinea Pig", J Cardiovasc Pharmacol 13(suppl. 5), 1989, p. 143-146.
Brunsveld et al. "Membrane binding of lipidated Ras peptides and proteins—The structural point of view", Biochimica et Biophysica Acta, 2009, vol. 1788, p. 273-288.
Cash et al., "Resolution of inflammation: targeting GPCRs that interact with lipids and peptides", Drug Discovery Today, 2014, vol. 19, No. 8, p. 1186-1192.
Cash et al. "Synthetic chemerin-derived peptides suppress inflammation through ChemR23", The Journal of Experimental Medicine, 2008, vol. 205, No. 4, p. 767-775.
Chamberlain et al., "Targeted delivery of Doxorubicin to mitochondria", ACS, Chem. Biol. 2013, vol. 8, p. 1389-1395.
Chan et al. "Modification of N-terminal α-amino groups of peptides and proteins using ketenes", Journal of the American Chemical Society, 2012, vol. 134, p. 2589-2598.
Chen, I. et al. "Site-specific labeling of cell surface proteins with biophysical probes using biotin ligase", Nature Methods, 2005, vol. 2, p. 99-104.
Cheng et al., "Luciferase reporter assay system for deciphering GPCR pathways", Curr Chem Genomics, 2010, vol. 4, p. 84-91.
Codelli, et al. "Second-Generation Difluorinated Cyclooctynes for Copper-Free Click Chemistry", J. Am. Chem. Soc. 2008, vol. 130, p. 11486-11493.
Conklin et al., "Substitution of three amino acids switches receptor specificity of Gq alpha to that of Gi alpha", Nature, 1993, vol. 363, p. 274-276.
Cuttitta et al., "Peptide amidation: signature of bioactivity", Anatomical Record 1993, vol. 236, p. 87-93.
Dafik, L. et al. "Fluorinated Lipid Constructs Permit Facile Passage of Molecular Cargo into Living Cells", J. Am. Chem. Soc., 2009, vol. 131, p. 12091-12093.
Debs et al., "Lung-specific delivery of cytokines induces sustained pulmonary and systemic immunomodulation in rats", J Immunol. 1988, vol. 140, p. 3482-3488.
Doyle J. R. et al. "Development of a Membrane-anchored Chemerin Receptor Agonist as a Novel Modulator of Allergic Airway Inflammation and Neuropathic Pain", Journal of Biological Chemistry, 2014, vol. 289, No. 19, p. 13385-13396.
Edwards and Price, "Role of Physiochemical Properties and Ligand Lipophilicity Efficiency in Addressing Drug Safety Risks", Annual Reports in Medicinal Chemistry, 2010, vol. 45, p. 380-391.
Eipper et al., "The biosynthesis of neuropeptides: peptide alpha-amidation", 1992, Annu Rev Neurosci 15:57-85.
Endo, H. "Resolving factors of inflammation—a bridge between Innate immunity and Adaptive immunity", Japanese Journal of Clinical Immunology, 2013, vol. 36, No. 3, p. 156-161. (English summary enclosed).

Fahy, J. "Eosinophilic and Neutrophilic Inflammation in Asthma", Proceedings of the American Thoracic Society, 2009, vol. 6, p. 256-259.
Fan et al., "Using luciferase assays to study G protein-coupled receptor pathways and a screen for GPCR modulators", Cell notes, 2005, vol. 13, p. 5-7.
Flatters and Bennett, "Ethosuximide reverses paclitaxel- and vincristine-induced painful peripheral neuropathy", Pain, 2004, vol. 109, p. 150-161.
Fortin et al., "Discovery of Dual-Action Membrane-Anchored Modulators of Incretin Receptors", PLoS One 2011, 6, e24693, 13 pages.
Fortin et al., "Membrane-Tethered Ligands are Effective Probes for Exploring Class B1 G Protein-Coupled Receptor Function", Proc. Natl. Acad Sci., 2009, vol. 106, p. 8049-8054.
Fortin et al., "The mu-opioid receptor variant N190K is unresponsive to peptide agonists yet can be rescued by small-molecule drugs", Mol. Pharmacol, 2010, vol. 78, p. 837-845.
Gautier, A. et al. "An Engineered Protein Tag for Multiprotein Labeling in Living Cells", Chem. & Biol. 2008, vol. 15, p. 128-136.
Gill, SC and Von Hippel, "Calculation of protein extinction coefficients from amino acid sequence data", Analytical Biochem, 1989, vol. 182, p. 319-326.
Gilmore J. et al. "N-Terminal Protein Modification through a Biomimetic Transamination Reaction", Angew. Chem. Int. Ed. 2006, vol. 45, p. 5307-5311.
Guan X. et al. "Understanding protein palmitoylation: Biological significance and enzymology", Sci China Chem., 2011, vol. 54, No. 12, p. 1888-1897.
Hamrah et al. "Alterations in Corneal Stromal Dendritic Cell Phenotype and Distribution in Inflammation", Arch Ophthalmol. 2003, vol. 121, p. 1132-1555.
Hang HC, "Exploring protein lipidation with chemical biology", Chem. Rev., 2011, vol. 111, p. 6341-6358.
Harwood et al., "Membrane Tethered Bursicon Constructs as Heterodimeric Modulators of the *Drosophila* G Protein-Coupled Receptor Rickets", Mol. Pharm., 2013, vol. 83, p. 814-821.
Hein et al. "Click Chemistry, a powerful tool for pharmaceutical sciences", Pharmaceutical Research, 2008, vol. 25, No. 10, p. 2216-2230.
Herova M. et al., "ChemR23, the receptor for chemerin and resolving E1, is expressed and functional on M1 but not on M2 macrophages", The Journal of Immunology, 2015, vol. 194, No. 5, p. 2330-2337.
Hesselink et al. "Resolvins and aliamides: lipid autacoids in ophthalmology—what promise do they hold?", Drug Design, Development and Therapy, 2016, vol. 10, p. 3133-3141.
Hubbard et al., "Anti-Neutrophil-Elastase Defenses of the Lower Respiratory Tract in a 1-Antitrypsin Deficiency Directly Augmented with an Aerosol of α 1-Antitrypsin", Annal Int Med 1989, vol. 3, p. 206-212.
Janeway, C. et al. "Principles of Innate and Adaptive immunity", Immunobiology: The Immune System in Health and Disease, 5th edition, 2001, 10 pages.
Jewett et al. "Rapid Cu-Free Click Chemistry with Readily Synthesized Biarylazacyclooctynones", J. Am. Chem. Soc. 2010, vol. 132, p. 3688-3690.
Katsuda et al. "A Small Molecule That Represses Translation of G-Quadruplex-Containing mRNA", J. Am. Chem. Soc. 2007, vol. 129, p. 9037-9043.
Kolb, H.C. et al. "Click Chemistry: Diverse Chemical Function from a Few Good Reactions", Angew. Chem. Int. Ed. 2001, 40, p. 2004-2021.
Kopin et al., "Identification of a series of CCK-2 receptor nonpeptide agonists: sensitivity to stereochemistry and a receptor point mutation", Proc Natl Acad Sci USA, 2003, vol. 100, p. 5525-5530.
Lagerstrom and Schioth, "Structural Diversity of G Protein-Coupled Receptors and Significance for Drug Discovery", Nat Rev Drug Discov, 2008, vol. 7, p. 339-357.
Langer R, "New Methods of Drug Delivery", Science, 1990, vol. 249, p. 1527-1533.
Lee et al., "The human brain cholecystokinin-B/gastrin receptor. Cloning and characterization", J Biol Chem 1993, vol. 268, p. 8164-8169.

(56) References Cited

OTHER PUBLICATIONS

Lipinski CA, "Lead- and Drug-Like Compounds: The Rule of Five Revolution", Drug Discovery Today, 2004, vol. 1, No. 4, p. 337-341.
Los, G.V. "HaloTag: A Novel Protein Labeling Technology for Cell Imaging and Protein Analysis", ACS Chem. Biol. 2008, vol. 3, p. 373-382.
"Medical Definition of Peptide", MedicineNet.com, 2017, 4 pages. http://www.medicinenet.com/script/main/art.asp?articlekey=24643, downloaded Mar. 14, 2017.
Meier, J. L.et al. "Synthesis and Evaluation of Bioorthogonal Pantetheine Analogues for in Vivo Protein Modification", Am. Chem. Soc. 2006, vol. 128, p. 12174-12184.
Missirilis D. et al. "Linker chemistry determines secondary structure of $p53_{14-29}$ in peptide amphiphile micelles", Bioconjugate Chemistry, 2010, vol. 21, p. 465-475.
Nadolski and Linder, "Protein lipidation", FEBS Journal, 2007, vol. 274, p. 5202-5210.
NCT00799552, "A Phase II, Multi-Center, Double-Masked, Randomized, Placebo Controlled, Study on the Safety and Efficacy of RX-10045 on the Signs and Symptoms of Dry Eye in Every Day Environmental Conditions and During Provocation Using the Controlled Adverse Environment (CAE) Model", ClinicalTrials.gov, 2010, 5 pages.
Ning et. Al. "Visualizing Metabolically Labeled Glycoconjugates of Living Cells by Copper-Free and Fast Huisgen Cycloadditions", Angew Chem Int Ed, 2008, vol. 47, p. 2253-2255.
Oeswein et al., "Aerosolization of Proteins Pharmaceuticals", Proceedings of Symposium on Respiratory Drug Delivery II, 1990, Keystone, Colorado, 34 pages.
Overington et al., "How Many Drug Targets Are There?", Nat Rev Drug Discov, 2006, vol. 5, p. 993-996.
Pachynski, R. et al. "The chemoattractant chemerin suppresses melanoma by recruiting natural killer cell antitumor defenses", Journal of Experimental Medicine, 2012, vol. 209, No. 8, p. 1427-1435.
Pap et al., "Peptide-based targeting of fluorophores to organelles in living cells", Exp. Cell Res., 2001, vol. 265, p. 288-293.
Pennington, M.W., "Hf cleavage and deprotection procedures for peptides synthesized using a Boc/Bzl strategy", Methods in Mol. Biol., 1994, vol. 35, p. 319-326.
Pisegna et al., "Molecular cloning, functional expression, and chromosomal localization of the human cholecystokinin type A receptor", Ann N Y Acad Sci, 1994, vol. 713, p. 338-342.
Popp, M. W. et al. "Sortagging: a versatile method for protein labeling", Nat. Chem. Biol. 2007, vol. 3, p. 707-708.
Rask-Andersen et al, "The Druggable Genome: Evaluation of Drug Targets in Clinical Trials Suggests Major Shifts in Molecular Class and Indication", Annu Rev Pharmacol Toxicol, 2013, vol. 54, p. 9-26.
Rostovtsev, V. V. et al. "A Stepwise Huisgen Cycloaddition Process: Copper(I)-Catalyzed Regioselective 'Ligation' of Azides and Terminal Alkynes", Angew. Chem. Int. Ed. 2002, vol. 41, p. 2596-2599.
Sawhney H S et al. "Bioerodible Hydrogels Based on Photopolymerized Poly(ethylene glycol)-co-poly(α-hydroxy acid) Diacrylate Macromers," Macromolecules, 1993, vol. 26, p. 581-587.
Schnolzer et al., "In situ neutralization in Boc-chemistry solid phase peptide synthesis. Rapid, high yield assembly of difficult sequences", International journal of peptide and protein research, 1992, vol. 40, p. 180-193.
Schuy S. et al. "Structure and Thermotropic phase Behavior of Fluorinated Phospholipid Bilayers: A combined Attenuated Total Reflection FTIR Spectroscopy and Imaging Ellipsometry Study", J. Phsy. Chem. B, 2008, vol. 112, p. 8250-8256.
Seo et al. "Docosahexaenoic acid selectively inhibits plasma membrane targeting of lipidated proteins ", FASEB Journal, 2006, vol. 20, p. 770-772.
Shimamura K. et al. "Identification of a stable chemerin analog with potent activity toward ChemR23", Peptides, 2009, vol. 30, No. 8, p. 1529-1538.
Sjödin et al., "Radioreceptor assay for formulations of salmon calcitonin", International Journal of Pharmaceutics, 1990, vol. 63, p. 135-144.
Sletten and Bertozzi, "Bioorthoganal Chemistry: Fishing for Selectivity in a Sea of Functionality", Angewandte Chemie International Edition, 2009, vol. 48, No. 38, p. 6974-6998.
Smith et al., "Pulmonary Deposition and Clearance of Aerosolized Alpha-I-Proteinase Inhibitor Administered to Dogs and to Sheep", J Clin Invest 1989, vol. 84, p. 1145-1146.
Song et al. "Novel peptide ligand directs liposomes toward EGF-R high-expressing cancer cells in vitro and in vivo", The FASEB Journal, 2009, vol. 23, p. 1396-1404.
Stallaert et al., Impedance Responses Reveal β2-Adrenergic Receptor Signaling Pluridimensionality and Allow Classification of Ligands with Distinct Signaling Profiles, PLoS One, 2012, vol. 7, No. 1:e29420.
Thirumurugan et al., "Click Chemistry for Drug Development and Diverse Chemical-Biology Applications", Am. Chem. Soc., 2013, vol. 113, p. 4905-4979.
Tornoe, C. W. et al. "Peptidotriazoles on Solid Phase: [1,2,3]-Triazoles by Regiospecific Copper(I)-Catalyzed 1,3-Dipolar Cycloadditions of Terminal Alkynes to Azides", J. Org. Chem. 2002, vol. 67, p. 3057-3062.
Triola G. "The Protein Lipidation and its Analysis", J. Glycom. Lipidom 2011, S12, 14 pages.
Valko K, "Application of High-Performance Liquid Chromatography Based Measurements of Lipophilicity to Model Biological Distribution", J. Chromatography, 2004, vol. 1037:(1-2), p. 299-301.
Wang, Q. et al. "Bioconjugation by Copper(I)-Catalyzed Azide-Alkyne [3+2] Cycloaddition", J. Am. Chem. Soc., 2003, vol. 125, p. 3192-3193.
Xu et al., "Resolvin E1 inhibits neuropathic pain and spinal cord microglial activation following peripheral nerve injury", J. Neuroimmune Pharmacol, 2013, vol. 8, p. 37-41.
Yildirim et al., "Drug-Target Network", Nat Biotechnol, 2007, vol. 25, p. 1119-1126.
Yoder et al. "Nanoscale Patterning in Mixed Fluorocarbon-Hydrocarbon Phospholipid Bilayers", J. Am. Chem. Soc. 2007, vol. 129, p. 9037-9043.
Zhang and Casey, "Protein prenylation: molecular mechanisms and functional consequences", Annu. Rev. Biochem., 1996, vol. 65, p. 241-269.
Zhang et al. "Converting peptides into drug leads by lipidation", Current Medicinal Chemistry, 2012, vol. 48, p. 6571-6584.
Zimmerman et al., "Differential b-Arrestin-Dependent Conformational Signaling and Cellular Responses Revealed by Angiotensin Analogs", Sci Signal, 2012, vol. 5(221):ra33, 13 pages.
Ahmed A.U., et al., "An Overview of Inflammation: Mechanism and Consequences," Front. Biol., 2011, vol. 6(4), pp. 274-281.
Ellis A., et al., "Neuroinflammation and the generation of neuropathic pain," British Journal of Anesthesia, 2013, vol. 111(1), pp. 26-37.
Abelson et al. "Neuropathic Pain: The Artifice of Dry Eye. A look at neuropathic pain and its relationship to dry-eye diagnosis and therapeutic strategies.", Review of Ophthalmology, 2016, 6 pages.

* cited by examiner

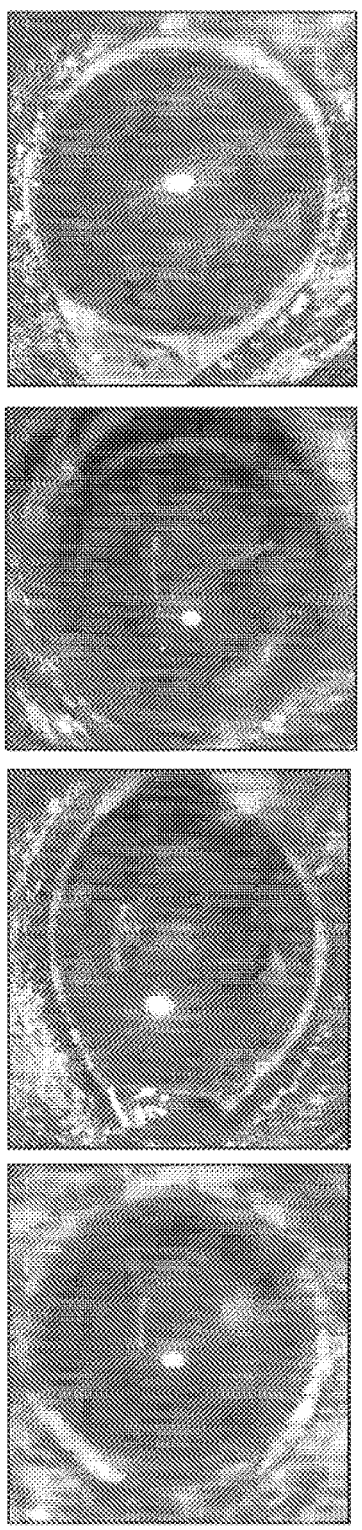
FIG. 10A Vehicle
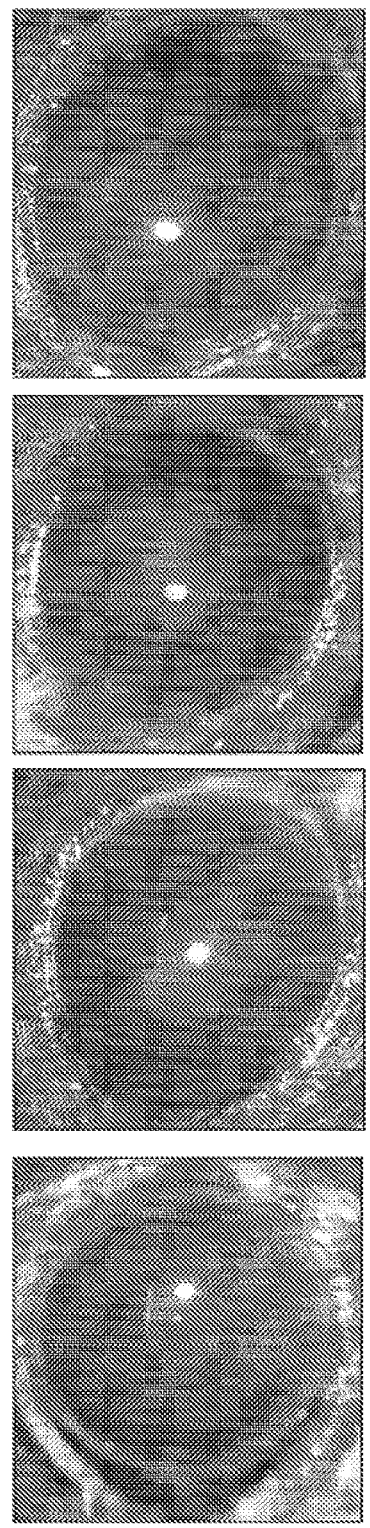
FIG. 10B OTTX-010

METHODS FOR TREATING SYMPTOMS OF DRY EYE DISEASE

RELATED APPLICATIONS

This application a continuation of U.S. application Ser. No. 16/070,467, filed on Jul. 16, 2018, which is a National Stage Application, filed under 35 U.S.C. 371, of International Application No. PCT/US2017/014605, filed on Jan. 23, 2017, which claims priority to U.S. provisional patent application No. 62/286,070, filed Jan. 22, 2016, the contents of each of these applications is incorporated by reference in its entirety.

INCORPORATION-BY-REFERENCE OF SEQUENCE LISTING

The contents of the text file named "OKYO_003_C01US Sequence Listing" which was created on Nov. 8, 2021 and is 3.7 KB in size, are hereby incorporated by reference in its entirety.

BACKGROUND OF THE DISCLOSURE

There is a variety of inflammatory conditions including, but not limited to, ocular inflammation, dry eye disease (DED), and ocular neuropathic pain.

Ocular inflammation can be caused by a microbial infection of the eye. Such infection may be fungal, viral, or bacterial. Ocular inflammation can also be caused by trauma, burn, autoimmune disease, chemical injury, contact lens, or other external stimuli. Neuropathic pain is a major health problem that occurs in as much as 7% of the general population. Up to 50% of patients do not respond to standard therapy.

DED is a multifactorial disease of the tears and the ocular surface with inflammation playing a part in its pathogenesis. Dry eye is a common and often chronic problem, particularly in older adults. In 2000, its prevalence in the US has been estimated around 17% in females and 12% in males but it has been increased in recent years and estimated to be more than 50%. People with dry eyes either do not produce enough tears or their tears are of a poor quality. Tears are produced by several glands in and around the eyelids. Tear production tends to diminish with age, with various medical conditions or as a side effect of certain medicines. Environmental conditions, such as wind and dry climates, can also decrease tear volume due to increased tear evaporation. When the normal amount of tear production decreases or tears evaporate too quickly from the eyes, symptoms of dry eye can develop. As for the quality of tears, tears are made up of three layers: oil, water and mucus. Each component protects and nourishes the front surface of the eye. A smooth oil layer helps prevent evaporation of the water layer, while the mucin layer spreads the tears evenly over the surface of the eye. If the tears evaporate too quickly or do not spread evenly over the cornea due to deficiencies with any of the three tear layers, dry eye symptoms can develop. The common form of dry eyes occurs when the water layer of tears is inadequate. This condition is also called keratoconjunctivitis sicca (KCS).

The present disclosure addresses the need of patients suffering from various inflammatory conditions including, but not limited to, ocular inflammation, DED, and ocular neuropathic pain.

SUMMARY OF THE DISCLOSURE

The present disclosure provides compositions and methods for treating or ameliorating at least one symptom of an inflammatory condition.

In one aspect, the present disclosure relates to a composition comprising (a) chemerin or a fragment or analog thereof and (b) a lipid entity linked to the chemerin or fragment or analog thereof.

In some embodiments, the lipid entity is linked to the chemerin or fragment or analog thereof through a linker. The linker can comprise polyethylene glycol, a peptide, or a combination thereof.

In some embodiments, the linker can be selected from the group consisting of:

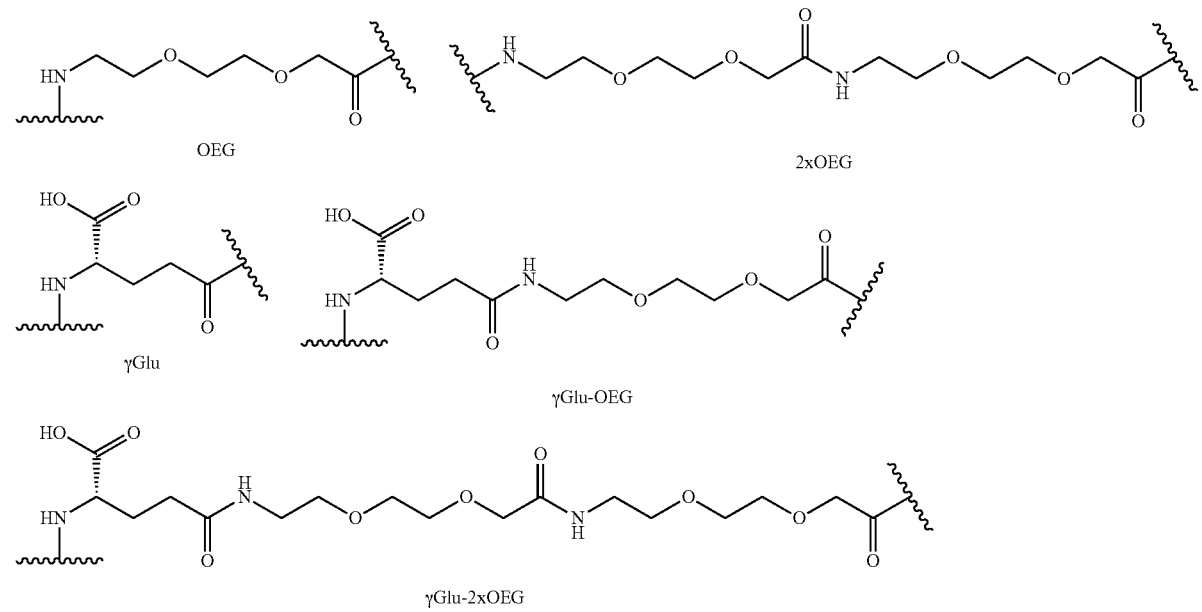

-continued
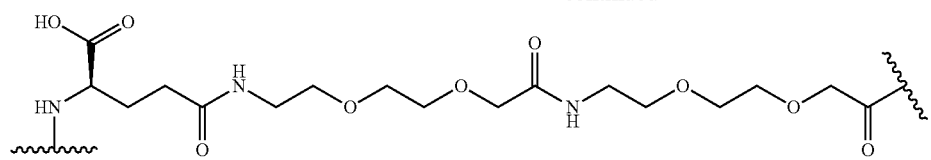
DγGlu-2xOEG
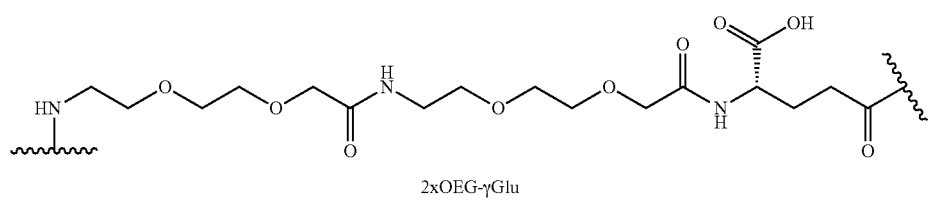
2xOEG-γGlu
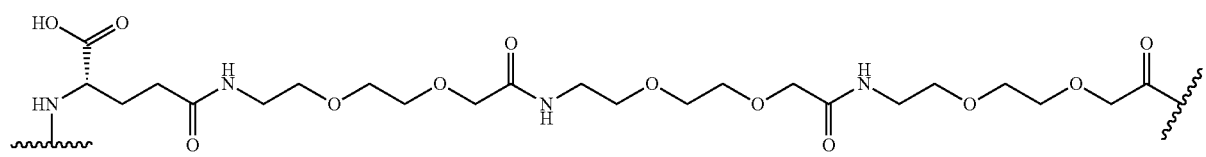
γGlu-3xOEG
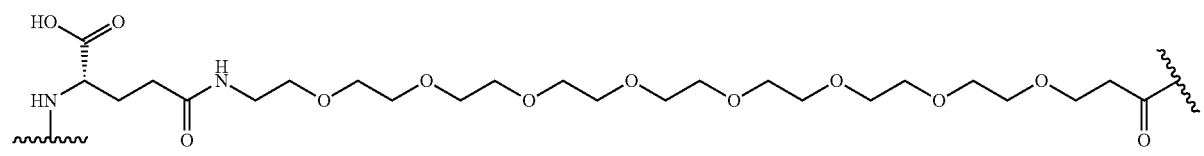
γGlu-8PEG
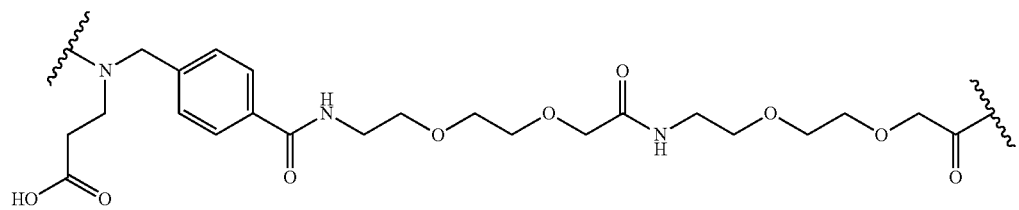
benzyl–βAla-2xOEG
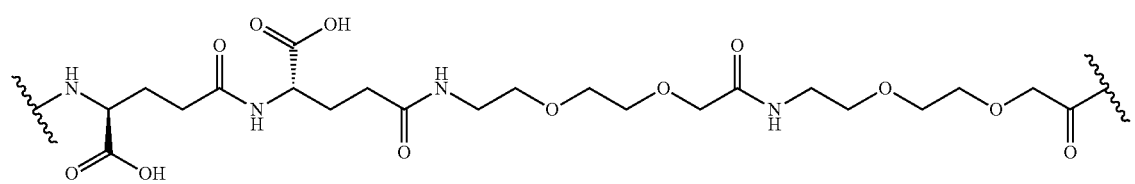
2xγGlu-2xOEG
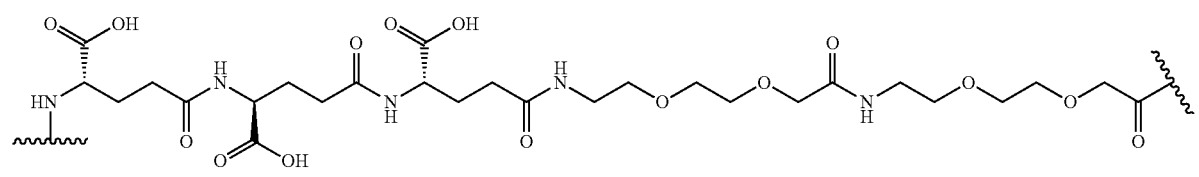
3xγGlu-2xOEG
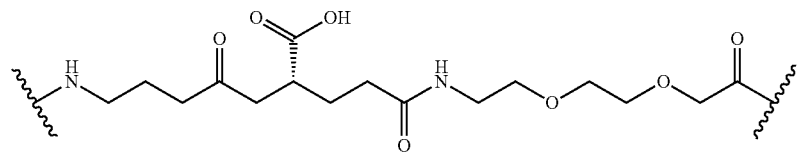
Abu-γGlu-OEG -continued

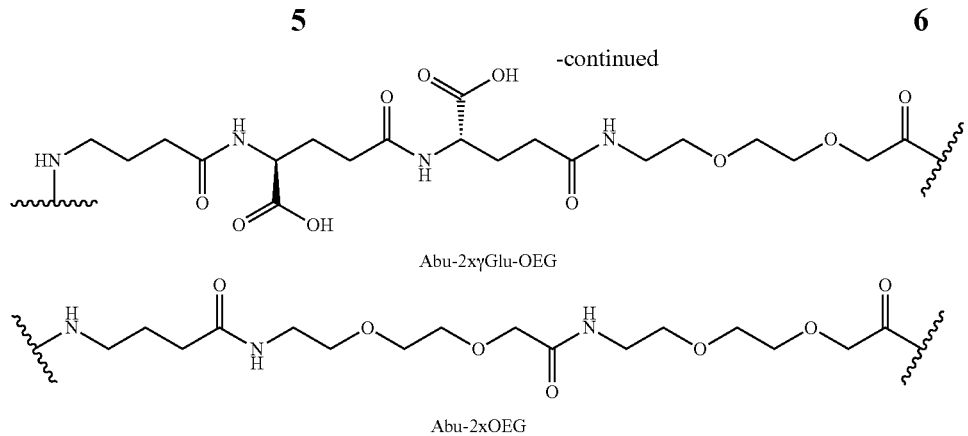

Abu-2xγGlu-OEG

Abu-2xOEG

In some embodiments, the chemerin fragment comprises at least 5 amino acids, at least 10 amino acids, at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 110 amino acids, at least 120 amino acids, at least 130 amino acids, at least 140 amino acids, or at least 150 amino acids, preferably of SEQ ID NO: 1. More preferably, the chemerin fragment retains CMKLR1 activation activity.

In some embodiments, the chemerin fragment has an amino acid sequence from position 21 to 157 of SEQ ID NO: 1. SEQ ID NO: 1 corresponds to the amino acid sequence of chemerin.

In some embodiments, the chemerin fragment comprises YFPGQFAFS (SEQ ID NO: 2).

In some embodiments, the chemerin analog is resistant to proteolysis. For example, the chemerin analog comprises YFLPSQFA-Tic-S(SEQ ID NO: 3), where the italicized Y, S, and A are D amino acids and Tic stands for 1,2,3,4-tetrahydroisoquinoline-3-carboxylic acid.

In some embodiments, the lipid entity is selected from the group consisting of α-linolenic acid, γ-linolenic acid, stearidonic acid, eicosapentaenoic acid, docosahexaenoic acid, linoleic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, mead acid, myristic acid, palmitic acid, stearic acid, 1,2-dipalmitoyl-sn-glycero-3-phosphoethanolamine (DPPE), GM1 ganglioside, GM2 ganglioside, GM3 ganglioside, 1,2-dipalmitoyl-sn-glycero-3-phosphocholine (DPPC), 1,2-dioleoyl-sn-glycero-3-phospho-L-serine (DOPS), 1,2-dioleoyl-sn-glycero-3-phosphocholine (DOPC), a glycosphingolipid, a sphingolipid, phosphatidylinositol 4,5-bisphosphate (PIP2), a ceramide, cholesterol, ergosterol, phytosterol, a hopanoid, and a steroid.

In some embodiments, the lipid entity is selected from the group consisting of α-linolenic acid, γ-linolenic acid, palmitic acid, vaccenic acid, oleic acid, and elaidic acid.

In some embodiments, the lipid entity can be linked at or near the N-terminus of the chemerin or fragment or analog thereof.

In some embodiments, the lipid entity can be linked at or near the C-terminus of the chemerin or fragment or analog thereof.

In another aspect, the present disclosure relates to a pharmaceutical composition comprising the composition of the present disclosure and a pharmaceutically acceptable carrier.

In yet another aspect, the present disclosure relates to a method of treating an inflammatory condition in a subject in need thereof, comprising administering to the subject a therapeutically effective amount of the pharmaceutical composition of the present disclosure or a composition comprising chemerin or a fragment or analog thereof.

In some embodiments, the inflammatory condition is ocular inflammation or dry eye disease.

In some embodiments, the pharmaceutical composition is administered topically.

In some embodiments, the pharmaceutical composition is administered once a day, twice a day, or thrice a day.

In some embodiments, the subject is a human.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

BRIEF DESCRIPTION OF THE DRAWINGS

FIGS. 10A-10B are photographs for clinical slit lamp exam 10 days after desiccation (dry eye disease (DED) mice). Vehicle is used in FIG. 10A. oTTx-010 is used in FIG. 10B. oTTx-010 stands for palmitate—PEG$_8$KGG-H$_2$N-Y*-F-L-P-S*-Q-F-A*-Tic-S-COOH (SEQ ID NO: 3), * denoting D amino acids and Tic stands for 1,2,3,4-tetrahydroisoquinoline-3-carboxylic acid.

DETAILED DESCRIPTION OF THE DISCLOSURE

CMKLR1 is a G protein-coupled receptor which has been shown to modulate nociception. This receptor is expressed in glia, dorsal root ganglion neurons, and immune cells. The endogenous ligand (agonist) for CMKLR1 is chemerin, a 163 amino acid protein. Chemerin, also known as retinoic acid receptor responder protein 2 (RARRES2), tazarotene-induced gene 2 protein (TIG2), or RAR-responsive protein TIG2 is a protein that in humans is encoded by the RARRES2 gene. The amino acid sequence of chemerin (*Homo sapiens*) is shown below in SEQ ID NO: 1.

```
                                          (SEQ ID NO: 1)
MRRLLIPLAL WLGAVGVGVA ELTEAQRRGL QVALEEFHKH

PPVQWAFQET SVESAVDTPF PAGIFVRLEF KLQQTSCRKR

DWKKPECKVR PNGRKRKCLA CIKLGSEDKV LGRLVHCPIE

TQVLREAEEH QETQCLRVQR AGEDPHSFYF PGQFAFSKAL PRS.
```

Figure 1:
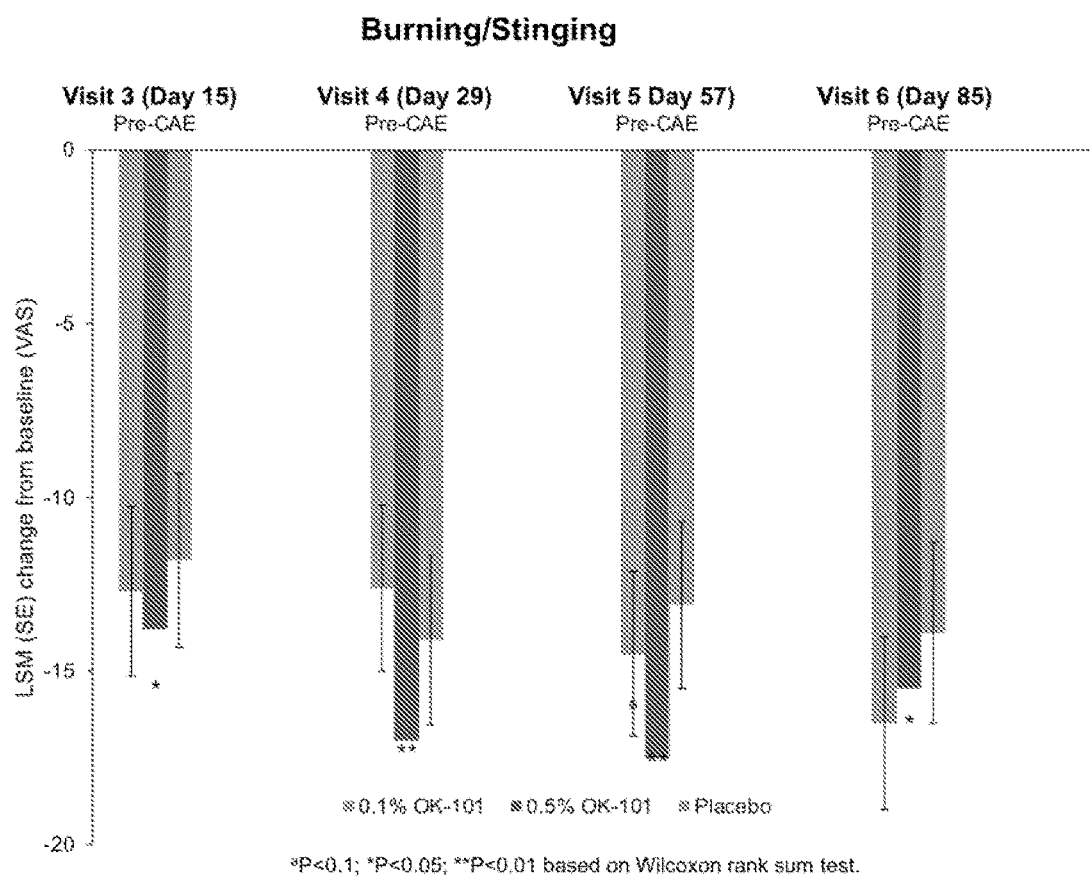
FIG. 1 is a schematic depicting the luciferase assay. HEK293 cells were transfected for 24 hours with cDNAs encoding: a) GPCR, b) a tethered ligand (where applicable), c) a luciferase reporter gene, and d) 0-galactosidase (transfection control). Luciferase activity was measured using Steadylite reagent. Luciferase data were normalized to 0-galactosidase values.
Figure 2:
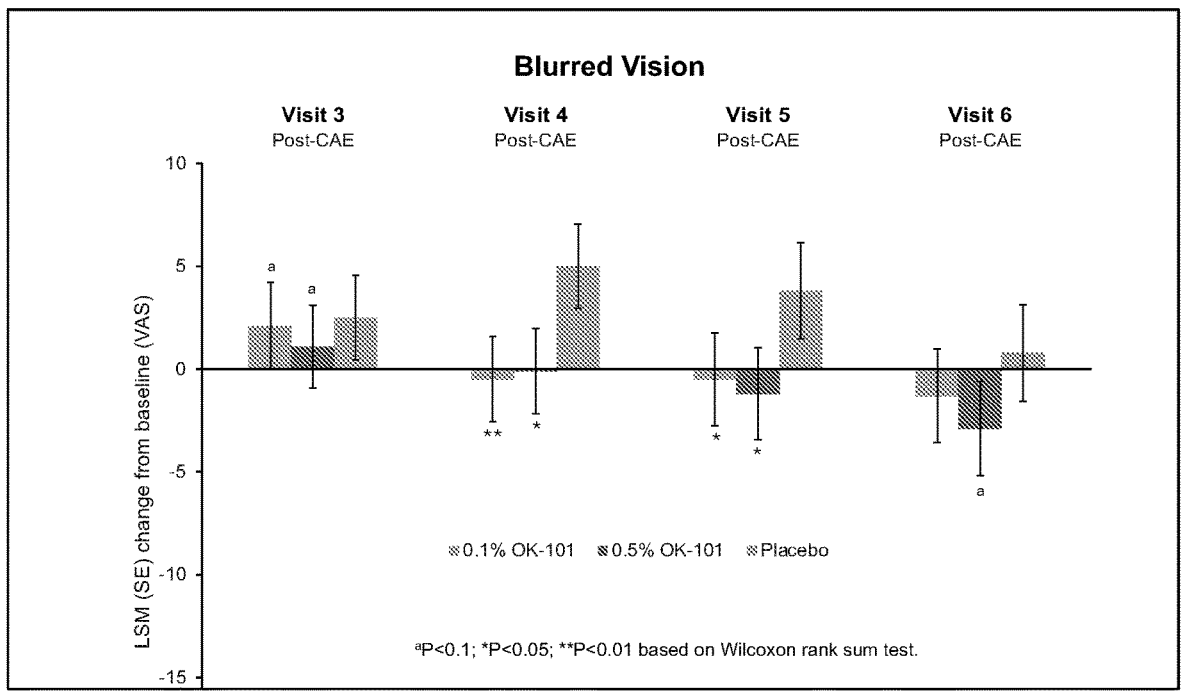
FIG. 2 is a set of schematics showing membrane tethered ligands (MTLs) and synthetic membrane anchored ligands (SMALs). (Left) MTLs are recombinantly expressed proteins that include a peptide ligand, an epitope tag, a linker sequence, and a transmembrane domain. (Right) SMALs are custom synthesized. Peptide ligands are conjugated to a PEG linker and a lipid to create synthetic MTL analogs. Due to their lipophilic properties SMALs anchor in the membrane when applied to cells.
Figure 3:
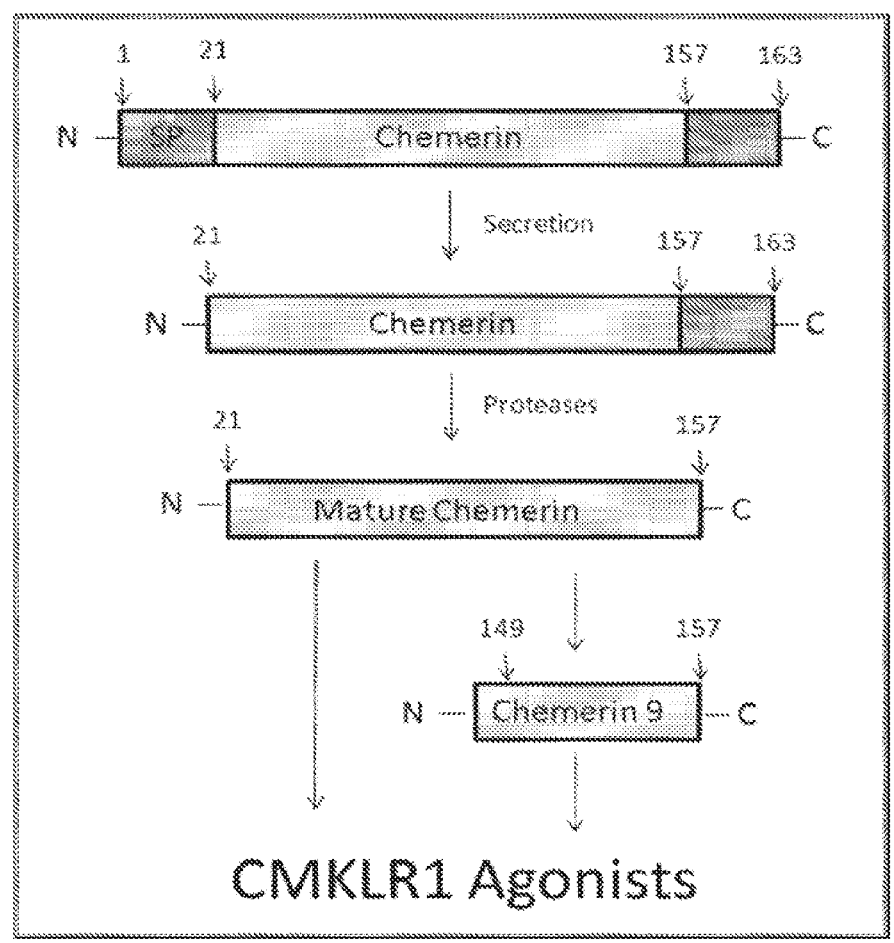
FIG. 3 is a schematic depicting chemerin peptide processing. Chemerin (1-163) is cleaved on both the N and C-terminus during endogenous processing to generate a mature peptide (21-157) which is a known agonist of the GPCR CMKLR1. A nine amino acid C-terminal fragment of chemerin (149-157) (SEQ ID NO: 2) has also been reported as an activator of CMKLR1. A series of chemerin peptides were incorporated into membrane tethered ligand constructs.
Figure 4A:
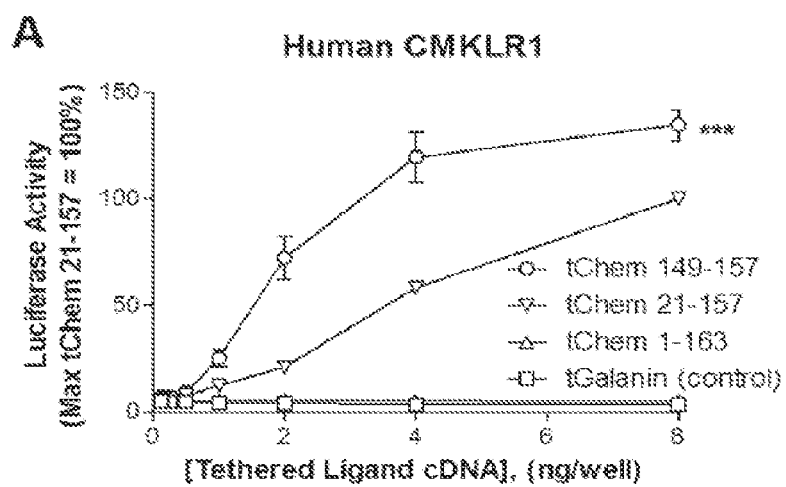
FIGS. 4A-4B are graphs showing that membrane tethered chemerin activates CMKLR1. Membrane tethered chemerin constructs encoding either mature chemerin (tChem21-157) or truncated chemerin (tChem149-157) both activate the (FIG. 4A) human CMKLR1 and (FIG. 4B) mouse CMKLR1.
Figure 4B:
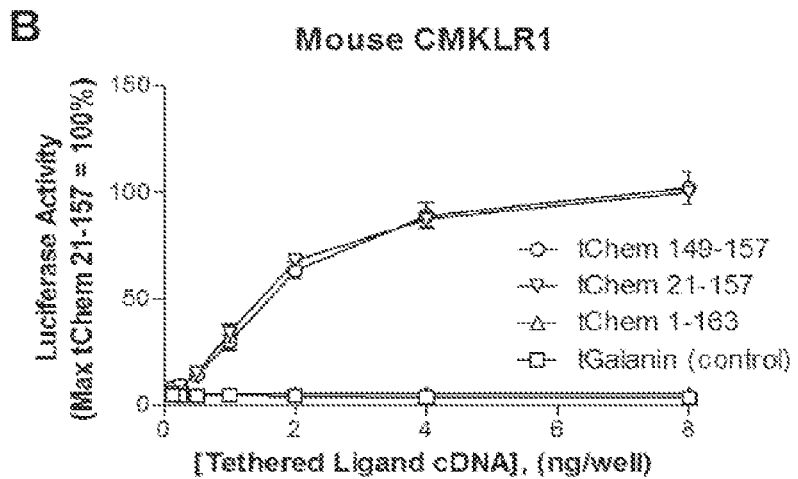
Figure 5A:
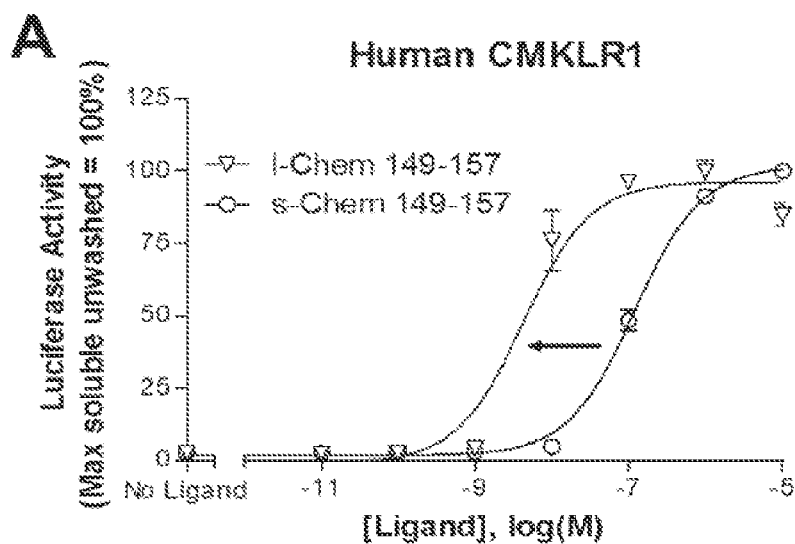
FIGS. 5A-5D are graphs showing the luciferase activity of l-Chem149-157 and s-Chem149-157. The lipidated chemerin peptide (l-Chem149-157) has enhanced potency on both human and mouse CMKLR1 compared to its soluble counterpart (FIGS. 5A, 5C). L-Chem149-157 anchors in the membrane conferring wash resistance compared to its soluble counterpart (s-Chem149-157) (FIGS. 5B, 5D).
Figure 5B:
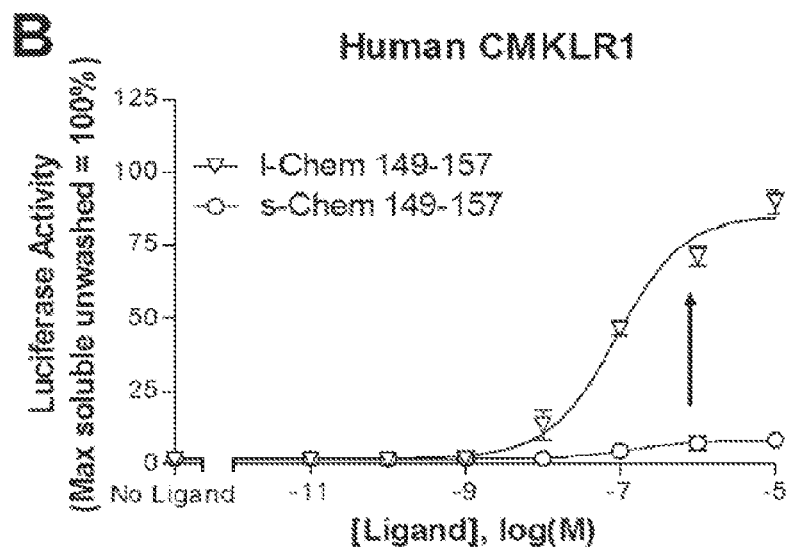
Figure 5C:
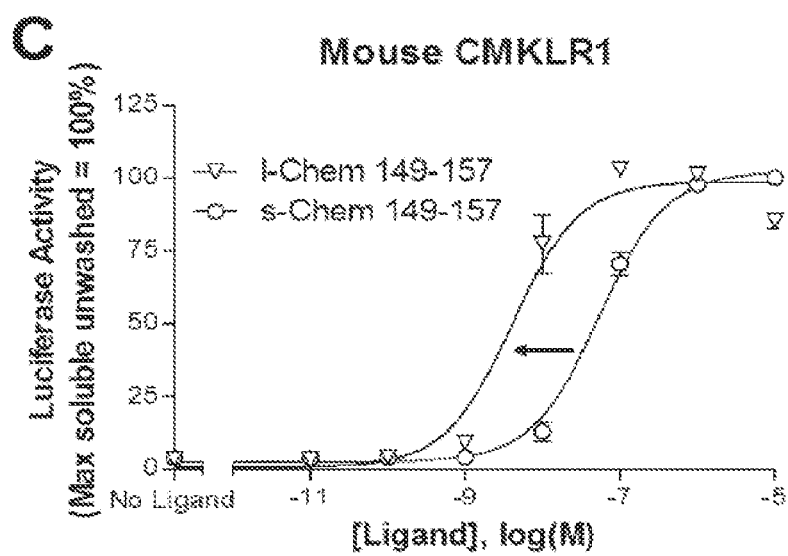
Figure 5D:
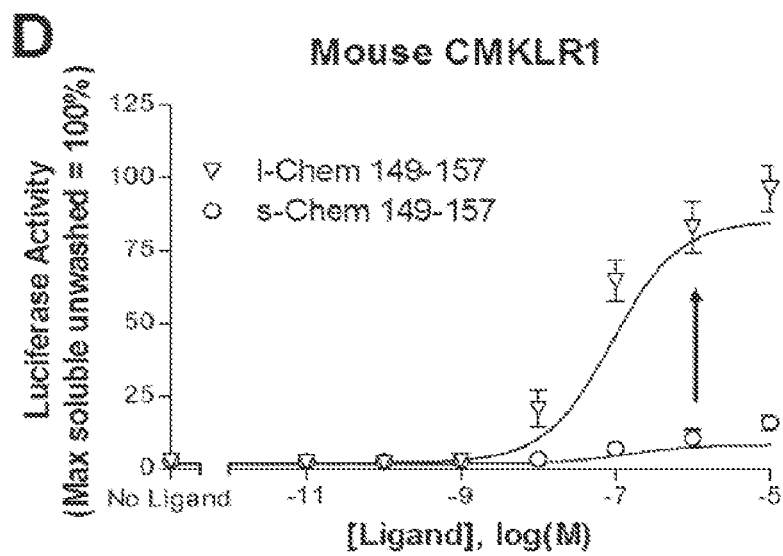

Chemerin is inactive as pre-prochemerin (having SEQ ID NO: 1) and is activated through cleavage of the C-terminus and N-terminus (FIG. 3) to form a chemerin fragment having an amino acid sequence from position 21 to 157 of SEQ ID NO: 1, which can function as an agonist for CMKLR1. This chemerin fragment has the following amino acid sequence:

```
                                          (SEQ ID NO: 4)
ELTEAQRRGL QVALEEFHKH PPVQWAFQET SVESAVDTPF

PAGIFVRLEF KLQQTSCRKR DWKKPECKVR PNGRKRKCLA

CIKLGSEDKV LGRLVHCPIE TQVLREAEEH QETQCLRVQR

AGEDPHSFYF PGQFAFS.
```

In one aspect, the present disclosure provides a composition comprising (a) chemerin or a fragment or analog thereof and (b) a lipid entity linked to the chemerin or fragment or analog thereof. Without wishing to be bound by theory, the pharmacological properties of chemerin or a fragment or analog thereof can be modulated by the choice of the lipid entity. In some embodiments, the composition of the present disclosure can function as an agonist of CMKLR1.

The chemerin fragment is a fragment of the amino acid sequence of SEQ ID NO: 1. The chemerin fragment can retain some or all of the biological functions of the amino acid sequence of SEQ ID NO: 4, e.g., functioning as an agonist of CMKLR1. In some embodiments, the chemerin fragment comprises at least 5 amino acids, at least 10 amino acids, at least 20 amino acids, at least 30 amino acids, at least 40 amino acids, at least 50 amino acids, at least 60 amino acids, at least 70 amino acids, at least 80 amino acids, at least 90 amino acids, at least 100 amino acids, at least 110 amino acids, at least 120 amino acids, at least 130 amino acids, at least 140 amino acids, or at least 150 amino acids. In some embodiments, the chemerin fragment comprises about 5-150 amino acids, about 5-120 amino acids, about 5-100 amino acids, about 5-80 amino acids, about 5-50 amino acids, or about 5-30 amino acids. In some embodiments, the chemerin fragment has an amino acid sequence from position 21 to 157 of SEQ ID NO: 1. In some embodiments, the chemerin fragment comprises YFPGQFAFS (SEQ ID NO: 2).

The chemerin analog can be an analog of either the full length or fragment of chemerin. The chemerin analog can retain some or all of the biological functions of the amino acid sequence of SEQ ID NO: 4, e.g., functioning as an agonist of CMKLR1. The chemerin analog can comprise at least one amino acid modification, at least two amino acid modifications, at least five amino acid modifications, or at least ten amino acid modifications. In some embodiments, the amino acid modification is amino acid substitution. The chemerin analog can be more resistant to proteolysis compared to the unmodified polypeptide. In some embodiments, the chemerin analog comprises YFLPSQFA-Tic-S(SEQ ID NO: 3), wherein the italicized Y, S, and A are D amino acids and Tic stands for 1,2,3,4-tetrahydroisoquinoline-3-carboxylic acid. The chemerin analog of SEQ ID NO: 3 is found to be resistant to proteolysis. See Shimamura et al., "Identification of a stable chemerin analog with potent activity toward ChemR23," Peptides 30, 2009, 1529-1538, the contents of which are incorporated by reference.

Any of a variety of lipid entities may be utilized in accordance with the present disclosure. According to various embodiments, a lipid entity can comprise an entity capable of insertion into a lipid bilayer (e.g., a cell membrane). In some embodiments, a lipid entity is capable of incorporating into a lipid raft in a lipid bilayer (e.g., a cell membrane).

In some embodiments, the lipid entity can comprise a saturated or unsaturated fatty acid. The numbers in the lipid name are used to describe the fatty acid chains on the lipid. The numbers are generally presented in the format (number of carbons in fatty acid chain): (number of double bonds in fatty acid chain), e.g., 16:0 would be 16 carbons in the fatty acid chain with zero double bonds. The saturated or unsaturated fatty acid can include at least 4 carbons, at least 5 carbons, at least 6 carbons, at least 7 carbons, at least 8 carbons, at least 9 carbons, at least 10 carbons, or at least 15 carbons in the fatty acid chain. In some embodiments, the saturated or unsaturated fatty acid can include about 4-24 carbons in the fatty acid chain. The number of double bonds in the fatty acid chain can be in the range of 0-10, e.g., 0-8, 0-6, 1-8, 1-6. For example, the lipid entity can be C22:0, C22:1, C22:2, C22:3, C22:4, C22:5, C22:6, C20:0, C20:1, C20:2, C20:3, C20:4, C20:5, C20:6, C18:0, C18:1, C18:2, C18:3, C18:4, C18:5, C18:6, C10:0, C10:1, C10:2, C10:3, C10:4, etc.

For example, the lipid entity can be selected from the group consisting of α-linolenic acid, γ-linolenic acid, stearidonic acid, eicosapentaenoic acid, docosahexaenoic acid, linoleic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, mead acid, myristic acid, palmitic acid, stearic acid, 1,2-dipalmitoyl-sn-glycero-3-phosphoethanolamine (DPPE), GM1 ganglioside, GM2 ganglioside, GM3 ganglioside, 1,2-dipalmitoyl-sn-glycero-3-phosphocholine (DPPC), 1,2-dioleoyl-sn-glycero-3-phospho-L-serine (DOPS), 1,2-dioleoyl-sn-glycero-3-phosphocholine (DOPC), a glycosphingolipid, a sphingolipid, phosphatidylinositol 4,5-bisphosphate (PIP2), a ceramide, cholesterol, ergosterol, phytosterol, a hopanoid, a steroid, fluorinated-GM1, fluorinated-GM2, and fluorinated-GM3. In some embodiments, the lipid entity can be α-linolenic acid. In some embodiments, the lipid entity can be γ-linolenic acid. In some embodiments, the lipid entity can be palmitic acid. In some embodiments, the lipid entity can be vaccenic acid. In some embodiments, the lipid entity can be oleic acid. In some embodiments, the lipid entity can be elaidic acid.

The attachment of a lipid entity to a polypeptide is referred to as lipidation. In some embodiments, lipidation may comprise N-myristoylation. As used herein, "N-myristoylation" refers to the attachment of a myristate to an N-terminal glycine.

In some embodiments, lipidation may comprise palmitoylation. As used herein "palmitoylation" refers to the creation of a thioester linkage of long-chain fatty acids on one or more cysteine residues present in a peptide or protein.

In some embodiments, lipidation comprises GPI-anchor addition. As used herein "GPI-anchor addition" refers to the linkage of glycosyl-phosphatidylinositol (GPI) to the C-terminus of a protein.

In some embodiments, lipidation comprises prenylation. As used herein "prenylation" refers to the creation of a thioether linkage of an isoprenoid lipid (e.g., farnesyl (C-15) or geranylgeranyl (C-20)) to a cysteine present in a peptide or protein. In some embodiments, lipidation comprises geranylation. In some embodiments, lipidation includes geranylgeranylation. In some embodiments, lipidation comprises the association of a ligand entity with any compound that is soluble in a cellular membrane (e.g., 10:1 in equilibrium constant $K_{assoc} \geq 10$).

In some embodiments, lipidation may comprise one or more of the following: attachment of diacylglycerol to the side chain of an N-terminal cysteine of a peptide or protein via the sulfur atom; attachment of O-octanoyl to a serine or threonine of a peptide or protein; and attachment of S-archaeol to a cysteine of a peptide or protein. In some embodiments, lipidation may occur, for example, at any lysine, glutamic acid, aspartic acid, serine, threonine, cysteine, and/or tyrosine. In some embodiments where a chemerin analog comprises one or more ornithine, lipidation may occur at any ornithine.

In some embodiments, the lipid entity can be linked at or near the N-terminus of chemerin or fragment or analog thereof. In some embodiments, the lipid entity can be linked at or near the C-terminus of chemerin or fragment or analog thereof.

In some embodiments, lipidation may include fluorination. Fluorination can include the addition of one or more $C_6F_{13}$ chains. Without wishing to be bound by theory, it is thought that the presence of one or more $C_6F_{13}$ chains may allow a lipid entity to segregate from hydrocarbon lipid membrane components (see *J. Am. Chem. Soc.* 2007, 129, 9037-9043; *J. Phsy. Chem. B*, 2008, 112, 8250-8256; *J. Am. Chem. Soc.*, 2009, 131, 12091-12093).

In some embodiments, the presence of at least one alkene in the structure of a lipid entity provides increased fluidity in a membrane (i.e., greater ability to move within the membrane) as compared to similar lipid entities lacking at least one alkene. In some embodiments, a lipid entity with greater fluidity is able to provide enhanced activity towards targets (e.g., receptors, ion channels, or enzymes) with a low density in a membrane. Without wishing to be bound by theory, it is possible that lipid entities with increased ability to move within a membrane are able to encounter a low density target faster than a lipid entity with less mobility within a membrane.

The composition of the present disclosure can optionally comprise a linker that links the lipid entity to chemerin or the fragment or analog thereof. For example, the linker can have a length of between about 2 Å and 175 Å, inclusive. In some embodiments, a linker is between 30 Å and 150 Å, inclusive.

In some embodiments, the linker can comprise a peptide. In some embodiments, a peptide linker is between about 2 and 20 amino acid residues in length. In some embodiments, a peptide linker is between about 5 and 10 amino acid residues in length. According to various embodiments, peptide linkers can be designed such that one or more α-helices are formed between chemerin or a fragment or analog thereof and a lipid entity. In some embodiments, a peptide linker may comprise a plurality of α-helices. In some embodiments, the plurality of α-helices is consecutive. In some embodiments, a plurality of α-helices is 2, 3, 4, 5, 6, 7, 8, 9, 10, 15, 20, or more α-helices.

In some embodiments, a peptide linker can comprise repeating units, for example a plurality of repeating glycine-asparagine (GN) units. In some embodiments, a peptide linker can comprise an epitope tag (e.g., a c-Myc tag) or other marker to allow for identification and/or characterization of provided agents and their fate in vitro and/or in vivo.

In some embodiments, the linker can comprise a non-peptide entity. In some embodiments, non-peptide linkers may be a synthetic polymer. According to various embodiments, the synthetic polymer may be any of a variety of lengths. In some embodiments, a linker comprising a synthetic polymer comprises a monomeric unit of the polymer. In some embodiments, a linker comprising a synthetic polymer comprises two or more monomeric units of a synthetic polymer (e.g., 2, 3, 4, 5, 6, 7, 8, 9, 10, 20, 30, 40, 50, 100 or more monomeric units).

In some embodiments, a linker can comprise at least one molecule of polyethylene glycol (PEG). Specific, non-limiting examples of suitable polymeric linkers include linkers with one or more monomeric units according to one of the following formulas:

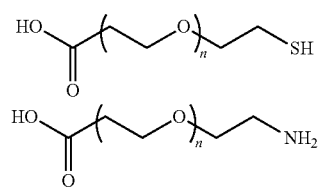

where n represents an integer greater than or equal to 1. In some embodiments, n is an integer between 2 and 50, 4 and 24, and/or 8 and 24, inclusive.

In some embodiments, the linker can have any one of the following structures:

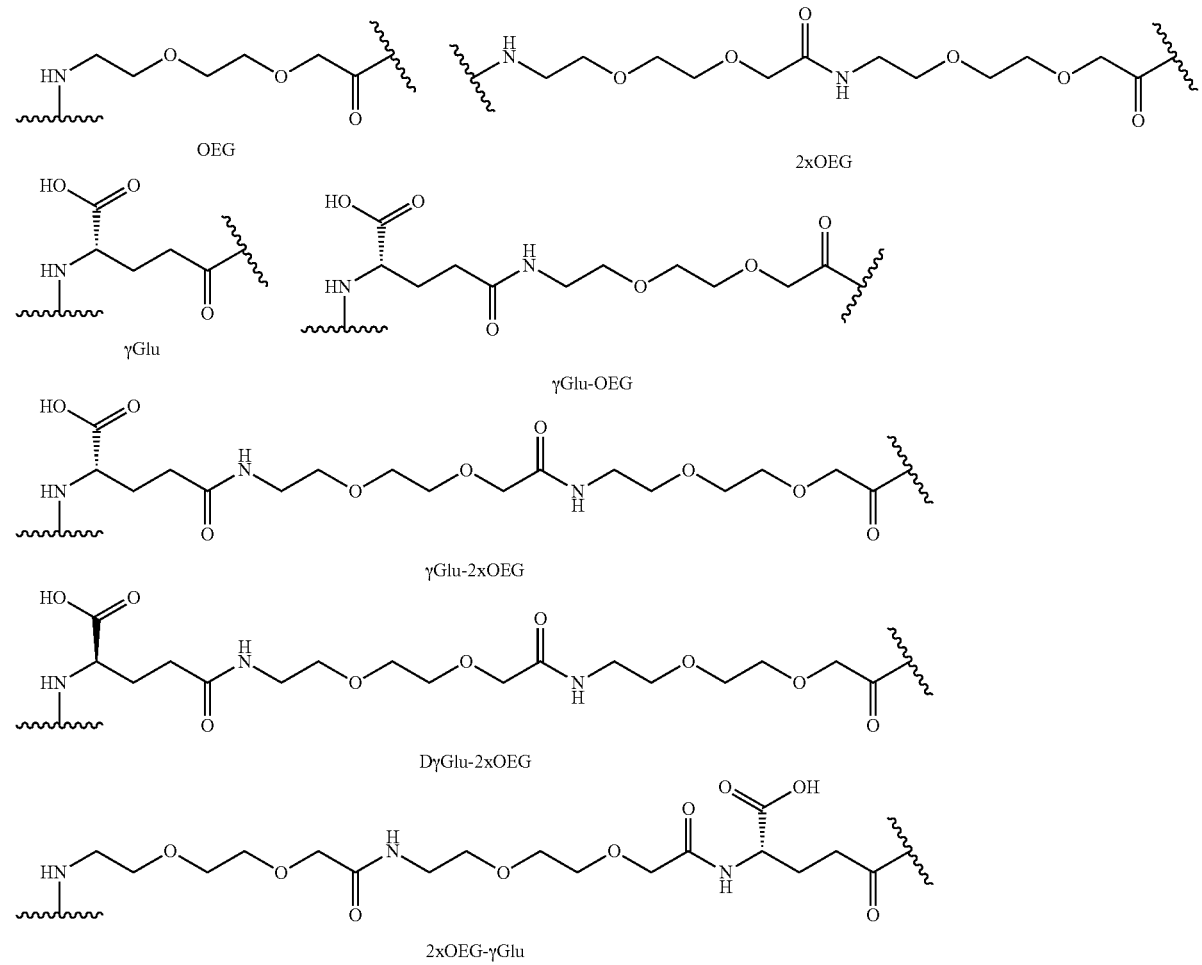

-continued
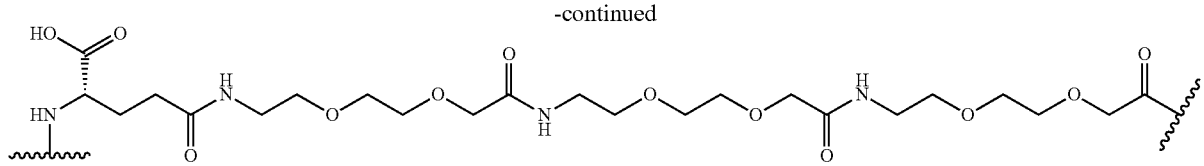
γGlu-3xOEG
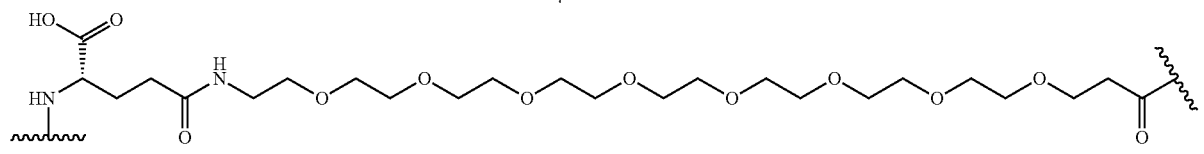
γGlu-8PEG
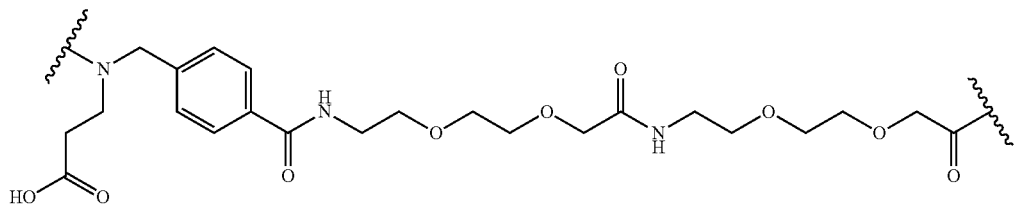
benzyl-βAla-2xOEG
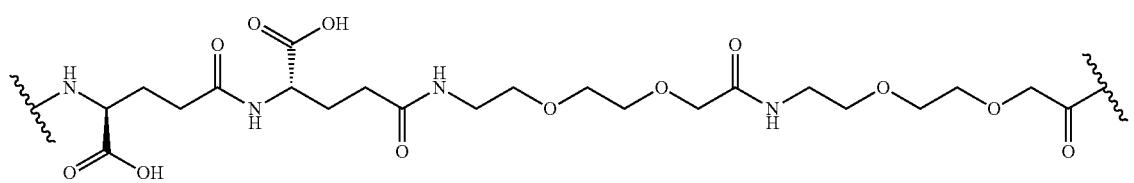
2xγGlu-2xOEG
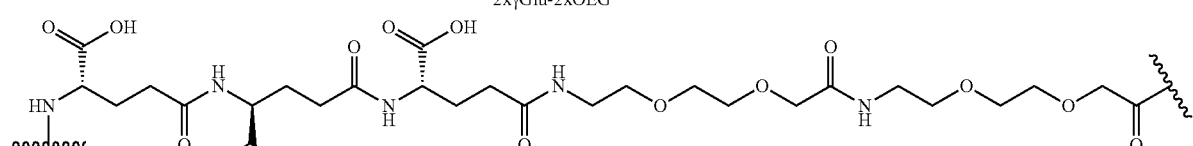
3xγGlu-2xOEG
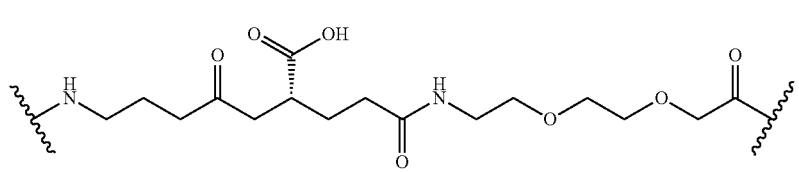
Abu-γGlu-OEG
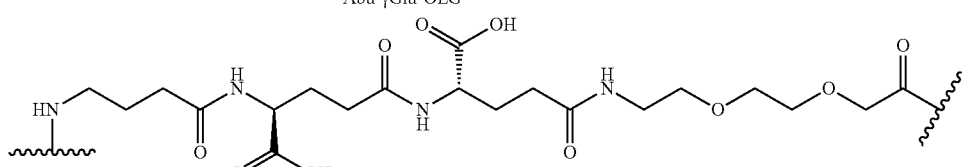
Abu-2xγGlu-OEG
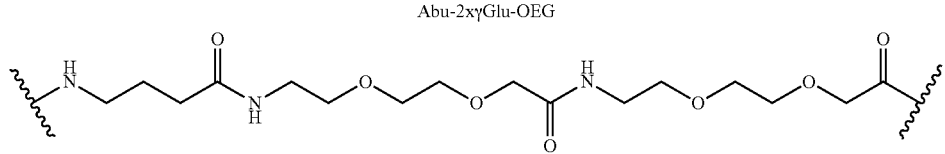
Abu-2xOEG In some embodiments, a linker can comprise 1-Ethyl-3-(3-Dimethylaminopropyl) carbodiimide (EDAC), Benzophenone-4-Isothiocyanate, Bis-((N-Iodoacetyl)Piperazinyl) Sulfonerhodamine, Succinimidyl 2-(2-Pyridyldithio) Propionate (SPDP), 4-Azido-2,3,5,6-Tetrafluorobenzoic acid (ATFB), (N-((2-Pyridyldthio)ethyl)-4-Azidosalicylamide), Succinimidyl trans-4-(maleimidylmethyl)cyclohexane-1-carboxylate (SMCC), and/or N-(t-BOC)-aminooxyacetic acid. Those of skill in the art will be able to identify additional candidate linkers according to known methods.

In some embodiments, a linker can comprise both a peptide and a non-peptide entity.

In some embodiments, a linker is formed, at least in part, as a result of a click reaction as further described below. In some embodiments, the click reaction is an azide-alkyne Huisgen cycloaddition reaction.

Additional examples of lipid entities, linkers, and methods of lipidation can be found at US20160052982, the contents of which are incorporated herein by reference.

The composition of the present disclosure can be formulated into a pharmaceutical composition, which can further comprise a pharmaceutically acceptable carrier. Techniques for formulation of the disclosed compositions can be found in *Remington: the Science and Practice of Pharmacy*, 19$^{th}$ edition, Mack Publishing Co., Easton, PA (1995). The pharmaceutical composition can be formulated for a variety of administration routes.

In some embodiments, the pharmaceutical composition can be formulated for topical administration. Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients.

In some embodiments, the pharmaceutical composition can be formulated for oral administration. Oral formulations containing the pharmaceutical composition described herein can be formulated into any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Methods of Treatment

The compositions described herein can be used to treat a variety of inflammatory conditions including, but not limited to, ocular inflammation, dry eye disease (DED), and ocular neuropathic pain.

In one aspect, the present disclosure provides a method of treating an inflammatory condition in a subject in need thereof, comprising administering to the subject a therapeutically effective amount of the pharmaceutical composition of the present disclosure or a composition comprising chemerin or a fragment or analog thereof.

In some embodiments, the inflammatory condition is ocular inflammation. In some embodiments, the ocular inflammation is uveitis. Uveitis is a wide range of inflammatory diseases of the eye, specifically the uvea. There are 3 basic layers of the eye—the sclera and cornea on the outside, the retina on the inside, and the uvea in between. The uvea is comprised mostly of blood vessels and connective tissue, including pigmented cells. The different parts of the uvea are the iris in the front, the ciliary body in the middle, and the choroid located behind these, which lies around most of the eye. Sometimes uveitis can affect parts of the eye other than uvea, such as retina, vitreous, or optic nerve. Types of uveitis are based on what part of the eye is affected. For example, anterior uveitis is the inflammation in the front of the eye, called iritis or iridocyclitis; intermediate uveitis is the inflammation in the middle part of the eye, or pars planitis or vitritis; posterior uveitis is the inflammation of the back of the eye, such as choroiditis, retinal vasculitis, retinitis, neuroretinitis, retinochoroiditis, or chorioretinitis.

Symptoms of uveitis commonly include redness, blurry vision, pain, light sensitivity, and floaters and flashes.

Ocular inflammation can be diagnosed through a review of illness history, slit lamp examination, blood work, or any combination thereof.

Current therapies for treating ocular inflammation include locally administered anti-cytokine or anti-inflammatory agents. In some embodiments, the pharmaceutical composition of the present disclosure or a composition comprising chemerin or a fragment or analog thereof can be administered in combination with an anti-cytokine or anti-inflammatory agent for treating ocular inflammation.

Anti-cytokine or anti-inflammatory agents include, but are not limited to, NF Kappa B inhibitors, for example corticosteroids, glucocorticoids such as flucinolonone; non-steroidal anti-inflammatory drugs (NSAIDs) such as sulindac and tepoxalin; antioxidants such as dithiocarbamate; and other compounds such as sulfasalazine [2-hydroxy-5-[-4-[C2-pyridinylamino)sulfonyl]azo]benzoic acid], clonidine, and autologous blood-derived products such as Orthokine.

In some embodiments, the inflammatory condition is DED. DED is primarily caused by the break-down of the pre-ocular tear film which results in dehydration of the exposed outer surface. People with DED may experience irritated, gritty, scratchy or burning eyes; a feeling of something in their eyes; excess watering; and blurred vision. The definition and classification of DED can be found at "The Definition and Classification of Dry Eye Disease: Report of the Definition and Classification Subcommittee of the International Dry Eye Workshop (2007)," the Ocular Surface 2007, Vol. 5, 75-92, the contents of which are incorporated herein by reference.

DED can be diagnosed through a comprehensive eye examination. Testing, with emphasis on the evaluation of the quantity and quality of tears produced by the eyes, may include: (a) patient history to determine the patient's symptoms and to note any general health problems, medications or environmental factors that may be contributing to the dry eye problem; (b) external examination of the eye, including lid structure and blink dynamics; (c) evaluation of the eyelids and cornea using bright light and magnification; and (d) measurement of the quantity and quality of tears for any abnormalities. Special dyes may be put in the eyes to better observe tear flow and to highlight any changes to the outer surface of the eye caused by insufficient tears.

Without wishing to be bound by theory, there is a rationale that ocular inflammation as a result of pro-inflammatory cytokines and growth factors plays a major role in the underlying causes of DED. As such, locally administered anti-cytokine or anti-inflammatory agents are often used in the treatment of DED. In some embodiments, the pharmaceutical composition of the present disclosure or a composition comprising chemerin or a fragment or analog thereof can be administered in combination with an anti-cytokine or anti-inflammatory agent for treating DED.

In some embodiments, the inflammatory condition is ocular neuropathic pain. Ocular neuropathic pain can be caused by inflammation. Therefore, it can be treated by the pharmaceutical composition of the present disclosure, optionally in combination with an anti-cytokine or anti-inflammatory agent. Neuropathic pain has typical symptoms like dysesthesias (spontaneous or evoked burning pain, often with a superimposed lancinating component), but the pain may also be deep and aching. Other sensations like hyperesthesia, hyperalgesia, allodynia (pain due to a normoxious stimulus), and hyperpathia (particularly unpleasant, exaggerated pain response) may also occur.

Methods of diagnosing inflammation in the eye can be found in Teoh and Dick, "Diagnostic techniques for inflammatory eye disease: past, present and future: a review," BMC Ophthalmology 2013, 13:41, the contents of which are incorporated herein by reference.

With respect to combination therapies involving a first therapeutic agent (e.g., a pharmaceutical composition of the present disclosure or a composition comprising chemerin or a fragment or analog thereof) and a second therapeutic agent (e.g., an anti-cytokine or anti-inflammatory agent), the first therapeutic agent can be administered concurrently with the second therapeutic agent; the first therapeutic agent can be administered before the second therapeutic agent; or the first therapeutic agent can be administered after the second therapeutic agent. The administrations of the first and second therapeutic agents can be separated by minutes or hours, e.g., about one hour, two hours, three hours, four hours, five hours, or six hours.

The therapeutically effective amount of a composition according to this disclosure can vary within wide limits and may be determined in a manner known in the art. For example, the composition can be dosed according to body weight. Such dosage will be adjusted to the individual requirements in each particular case including the specific compound(s) being administered, the route of administration, the condition being treated, as well as the patient being treated. In another embodiment, the drug can be administered by fixed doses, e.g., dose not adjusted according to body weight. In general, a daily dosage of from about 0.5 mg to about 1000 mg should be appropriate, although the upper limit may be exceeded when indicated. The dosage can be from about 5 mg to about 500 mg per day, e.g., about 5 mg to about 400 mg, about 5 mg to about 300 mg, about 5 mg to about 200 mg. The daily dosage can be administered as a single dose or in divided doses, or for parenteral administration it may be given as continuous infusion. The pharmaceutical composition or a composition comprising chemerin or a fragment or analog thereof can be administered once a day, or several times a day, e.g., twice a day, or thrice a day.

A therapeutically effective amount of a composition is that which provides an objectively identifiable improvement as noted by the clinician or other qualified observer.

In some embodiments, a therapeutically effective amount for treating ocular inflammation is an amount that reduces the extent of inflammation in the subject by at least 10%, at least 20%, at least 30%, at least 40%, at least 50%, at least 60%, at least 70%, at least 80%, at least 90%, or at least 95% compared to a placebo.

In some embodiments, a therapeutically effective amount for treating DED is an amount that increases the production of tears in the subject by at least 10%, at least 20%, at least 30%, at least 40%, at least 50%, at least 60%, at least 70%, at least 80%, at least 90%, at least 100%, or at least 150% compared to a placebo.

The pharmaceutical compositions can be included in a container, pack, or dispenser together with instructions for administration. The compositions described herein can be administered orally, nasally, transdermally, pulmonary, inhalationally, buccally, sublingually, intraperintoneally, subcutaneously, intramuscularly, intravenously, rectally, intrapleurally, intrathecally, topically, or parenterally. In one embodiment, the composition is administered topically. For example, the composition is administered in the form of eye drops. One skilled in the art will recognize the advantages of certain routes of administration.

The dosage regimen utilizing the compositions described herein is selected in accordance with a variety of factors including species, ethnicity, age, weight, sex and medical condition of the patient; the severity of the condition to be treated; the route of administration; the renal and hepatic function of the patient; and the particular composition employed. An ordinarily skilled physician or veterinarian can readily determine and prescribe the effective amount of the drug required to prevent, counter, or arrest the progress of the condition.

Definitions

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein. It is to be understood that the terminology used herein is for the purpose of describing particular embodiments only, and is not intended to be limiting.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetic). Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxyl terminus. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is C1-C4 alkyl). The term peptide also includes modifications, such as but not limited to those described above, of amino acids falling between the amino and carboxy termini. The term peptide can also include peptides modified to include one or more detectable labels.

The phrase "amino acid residue" as used herein refers to an amino acid that is incorporated into a peptide by an amide bond or an amide bond mimetic.

The terminal amino acid at one end of the peptide chain typically has a free amino group (i.e., the amino terminus or N terminus). The terminal amino acid at the other end of the chain typically has a free carboxyl group (i.e., the carboxy terminus or C terminus). Typically, the amino acids making up a peptide are numbered in order, starting at the amino terminus and increasing in the direction of the carboxy terminus of the peptide.

As used herein, the term "analog" refers to a variant or mutant polypeptide having one or more amino acid modifications compared to the wild type.

As used herein, an "amino acid modification" refers to a change in the amino acid sequence of a predetermined amino acid sequence. Exemplary modifications include an amino acid substitution, insertion and/or deletion. An "amino acid modification at" a specified position, e.g. of chemerin or a fragment thereof, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Iie): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Ellman et al., supra, can be used. Briefly, these procedures involve chemically activating a suppressor tRNA with a non-naturally occurring amino acid residue followed by in vitro transcription and translation of the RNA. In some embodiments, an L amino acid can also be substituted by a D amino acid.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "pharmaceutical composition" refers to a mixture of a compound disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers, preservatives, and adjuvants.

As used herein, the terms "treat," "treating," "treatment," and the like refer to reducing or ameliorating a disorder and/or a symptom associated therewith. It will be appreciated that, although not precluded, treating a disorder or condition does not require that the disorder or symptom associated therewith be completely eliminated. The terms "treat," "treating," or "treatment," do not include prevention.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

As used herein, a "subject" can be any mammal, e.g., a human, a non-human primate, mouse, rat, dog, cat, cow, horse, pig, sheep, goat, camel. In a preferred embodiment, the subject is a human.

As used herein, a "subject in need thereof" is a subject having an inflammatory condition.

As used herein, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "a device" includes one or more devices, and the like. Unless specifically stated or obvious from context, as used herein, the term "or" is understood to be inclusive and covers both "or" and "and".

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" when used in conjunction with numerical values and/or ranges generally refers to those numerical values and/or ranges near to a recited numerical value and/or range. In some instances, the term "about" can mean within ±10% of the recited value. For example, in some instances, "about 100 [units]" can mean within ±10% of 100 (e.g., from 90 to 110).

EXAMPLES

Example 1

Abbreviations: s-Chem 21-157 (soluble recombinant human chemerin corresponding to amino acids 21-157); s-Chem 149-157 (soluble C-terminal 9 amino acids of human chemerin); l-Chem 149-157 (lipidated C-terminal 9 amino acids of human chemerin); s-Stable Chem (soluble stable chemerin peptide; l-Stable Chem (lipidated stable chemerin peptide).

One emerging treatment strategy to treat neuropathic pain is to target modulators of the neuroinflammatory process which contributes to neuropathic pain. We have previously identified a palmitoylated stable analog ("C16-Stable Chem9") derived from a 9 amino acid fragment of chemerin. This analog anchors to the cell membrane resulting in high potency and long-term activity. When assessed in vivo, palm sC9 alleviated neuropathic pain in a mouse model of chronic constriction injury. Extending from these observations, we hypothesized that the pharmacological properties of our peptide may be further optimized by modifying the lipid anchor. We have chemically synthesized a series of Chem 9 analogs with various lipid tails (e.g. cholesterol, oleic acid, linolenic acid). In vitro pharmacological characterization of each peptide was done using HEK293 cells transiently expressing the recombinant CMKLR1. We have found that varying the lipid tail of the ligand significantly alters agonist potency of chemerin 9 analogs (within a 30-fold range). Furthermore, selected lipid tails bias binding to either albumin (thus enhancing systemic delivery) or to the cellular membrane (which favors locally restricted function). The lipidated CMKLR1 ligands have promise as modulators of neuropathic pain. In addition, our findings illustrate an approach where serial addition/substitution of lipid anchors can be applied to optimize the pharmacological as well as pharmacokinetic properties of many peptide ligands.

CMKLR1 fl-Arrestin recruitment was assessed following a 1 hr treatment with stable Chem 9 analogs (FIGS. 9A-9D).

Chemerin a 136 amino acid protein can be truncated to a 9 amino acid peptide which is active as either a membrane tethered ligand (MTL) or a lipidated peptide.

Figure 6A:
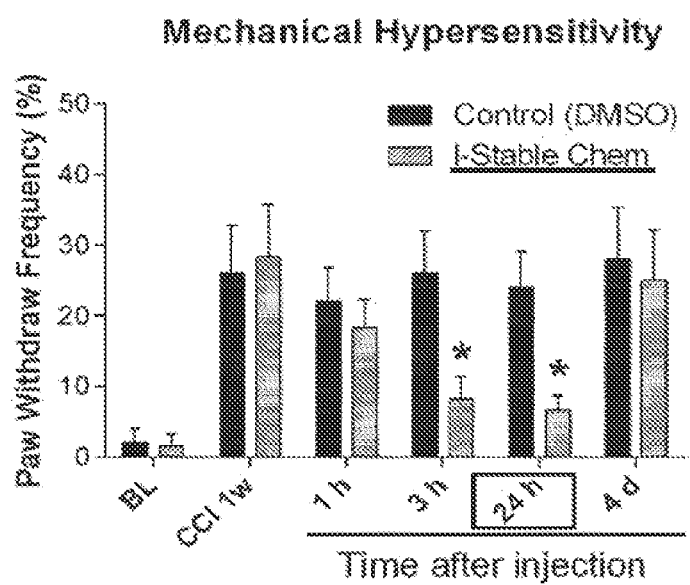
FIGS. 6A-6B are graphs showing that CMKLR1 agonists C16-stable Chem9 and Resolvin E1 abrogate neuropathic pain in a chronic constriction injury (CCI) mouse model. Following intrathecal administration of compound, 1-Stable Chem (C16-stable Chem9) blocked mechanical hypersensitivity for more than 24 hours after compound administration (FIG. 6A). In contrast, Resolvin E1 lost efficacy by 3 hours post injection (FIG. 6B).
Figure 6B:
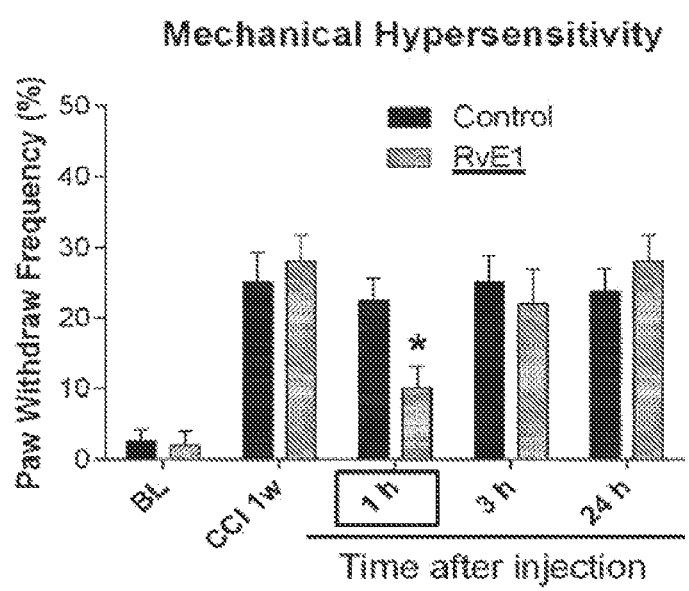
Figure 7:
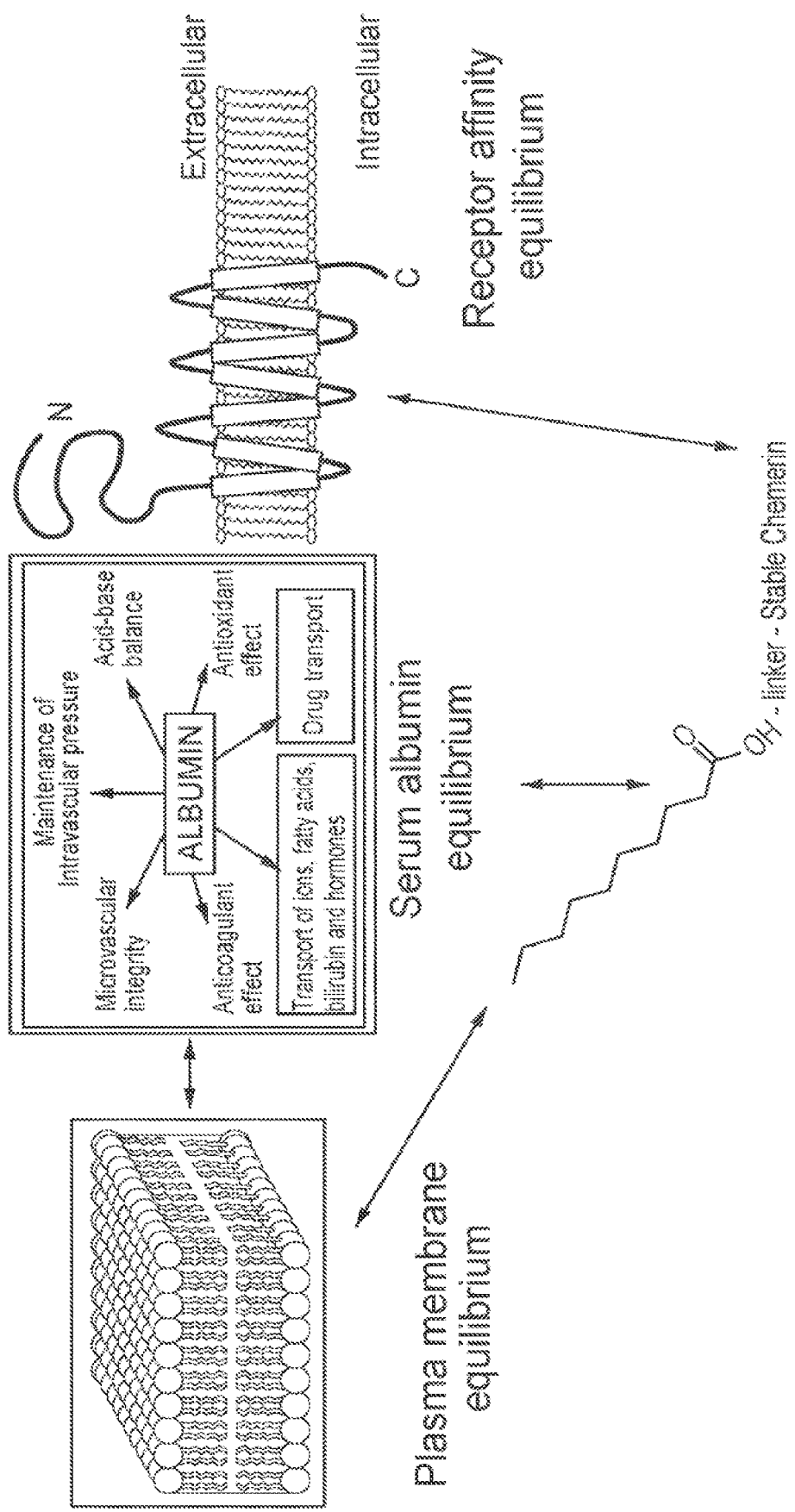
FIG. 7 shows lipidated peptide equilibrium. In addition to peptide affinity for its cognate receptor CMKLR1, in the context of systemic administration, lipidated peptides may also bind to both the plasma membrane and serum albumin. Changing the lipid tail therefore could alter the equilibrium between these various bound states.
Figure 8A:
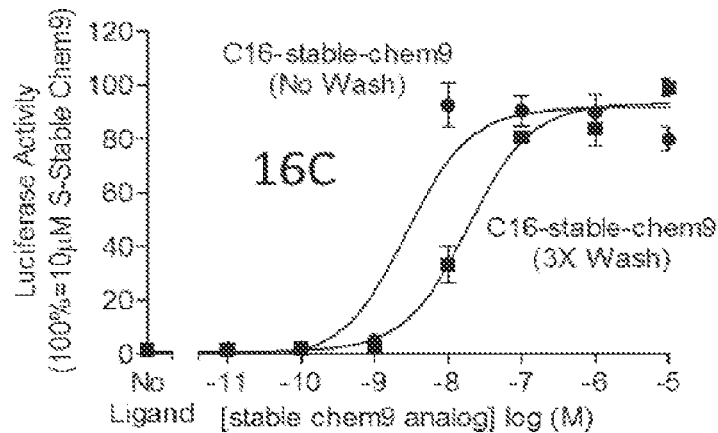
FIGS. 8A-8D are graphs showing that bovine serum albumin (BSA) differentially alters the pharmacological properties of lipidated stable Chemerin 9 analogs. Wash resistance (an index of membrane adherence) of palmitic acid stable Chem9 is decreased in the presence of BSA (FIGS. 8A-8B). With a linolenic acid (18C:3) stable Chem 9 analog, activity is further reduced (FIGS. 8C-8D) after washing in the presence of BSA.
Figure 8B:
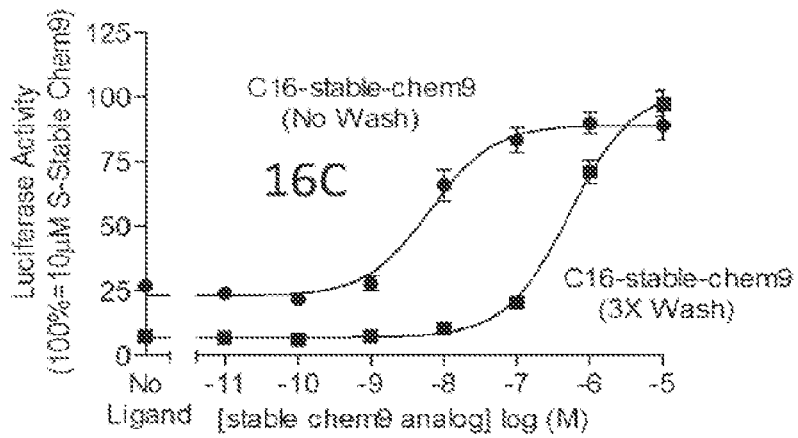
Figure 8C:
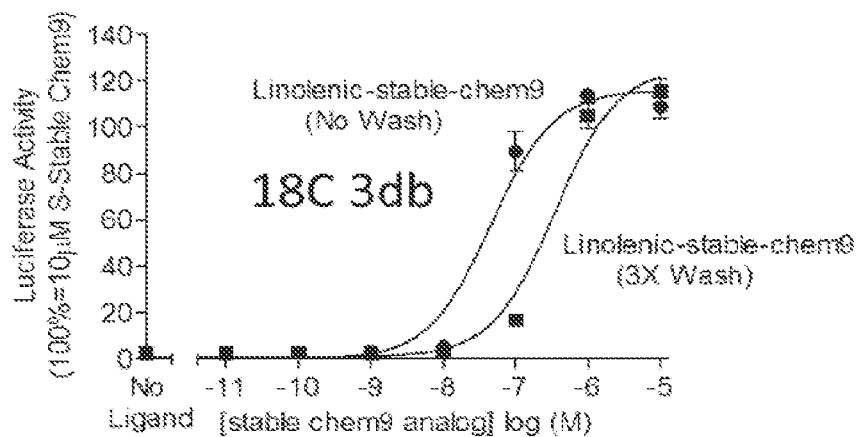
Figure 8D:
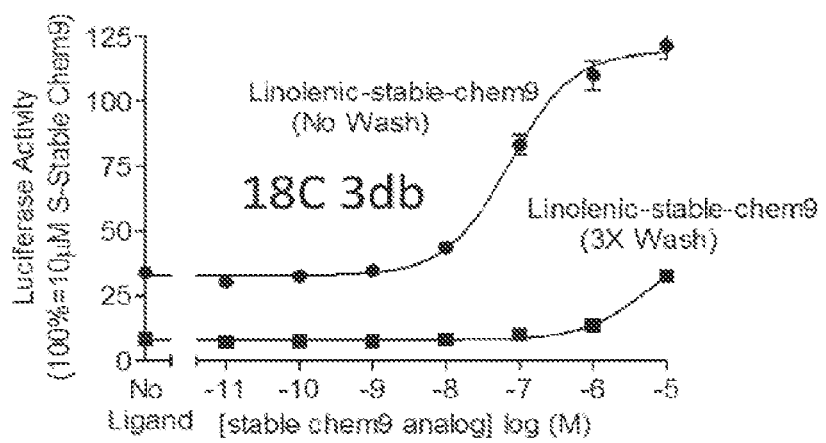
Figure 9A:
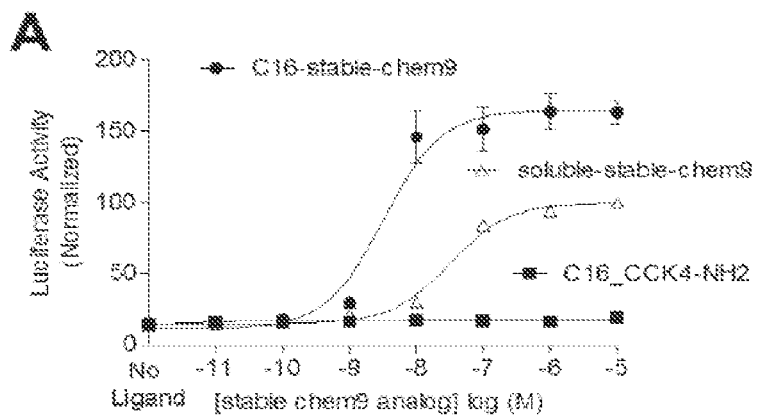
FIGS. 9A-9D are graphs showing that 0-Arrestin recruitment following stimulation with lipidated stable chemerin 9 analogs. Potency and maximum efficacy are altered by lipid tail substitution. Activity was assessed using a Link-Light™ CMKLR1 stable cell line which measures 0-Arrestin recruitment.
Figure 9B:
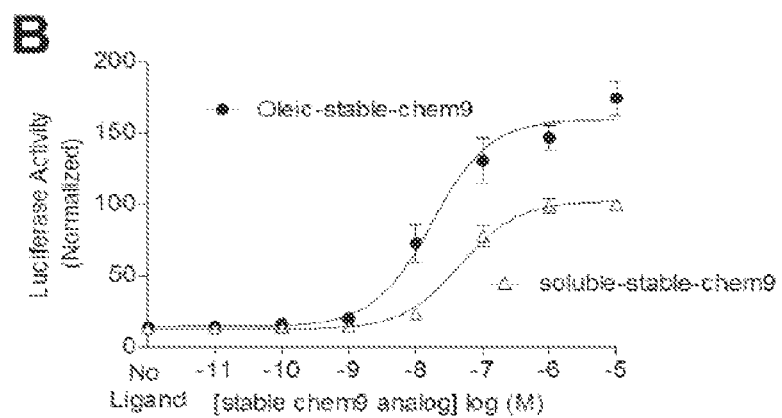
Figure 9C:
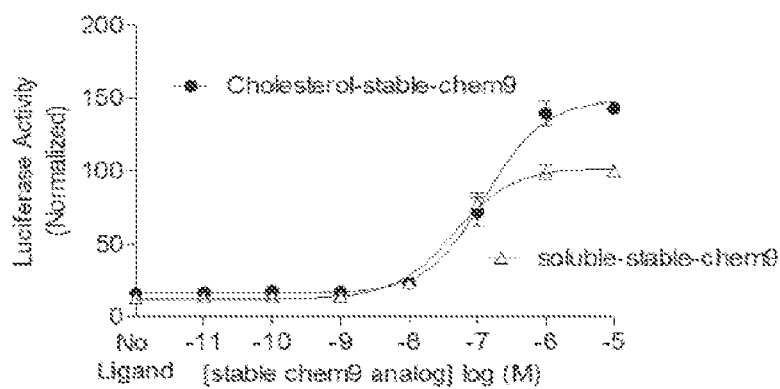
Figure 9D:
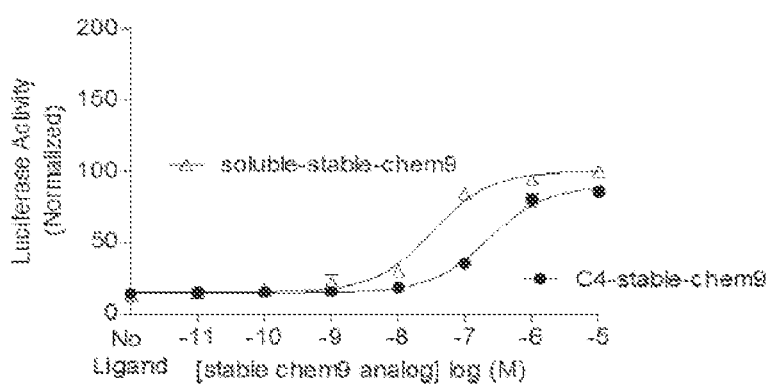
Figure 11:
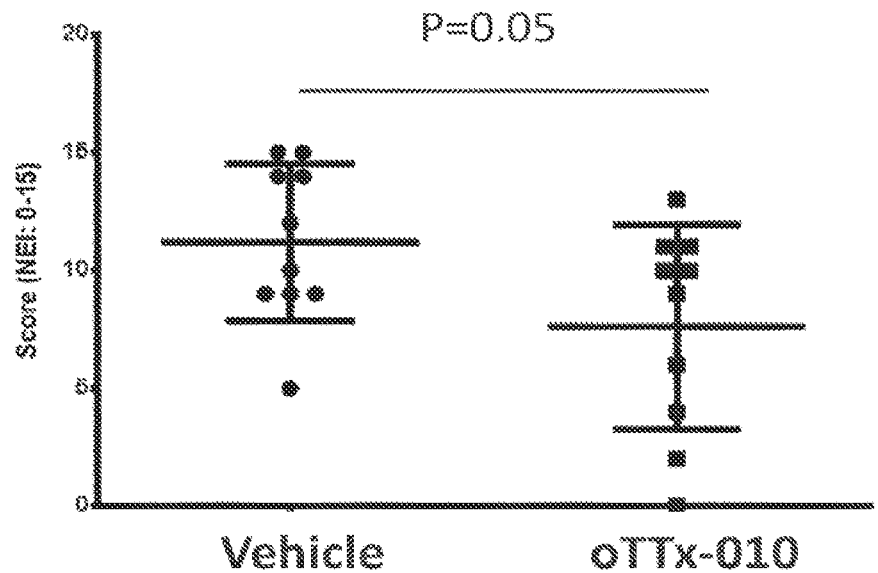
FIG. 11 is a graph showing that corneal fluorescein staining scores were lower in DED mice treated with oTTx-010. NEI scoring system: 0-15.
Figure 12:
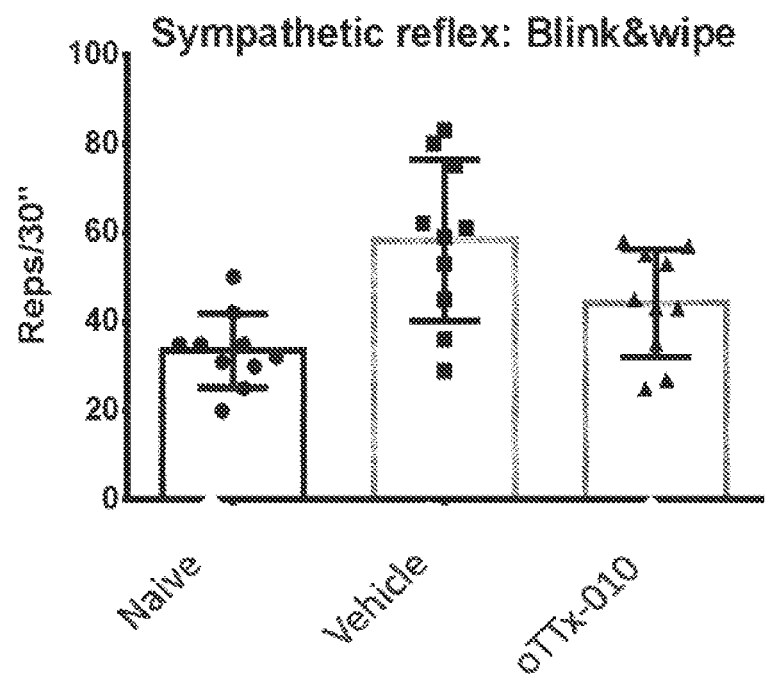
FIG. 12 is a graph showing that blink reflex as a sign of ocular irritation was significantly lower in the oTTx-010 treated group as compared to vehicle treated group of DED mice.
Figure 13:
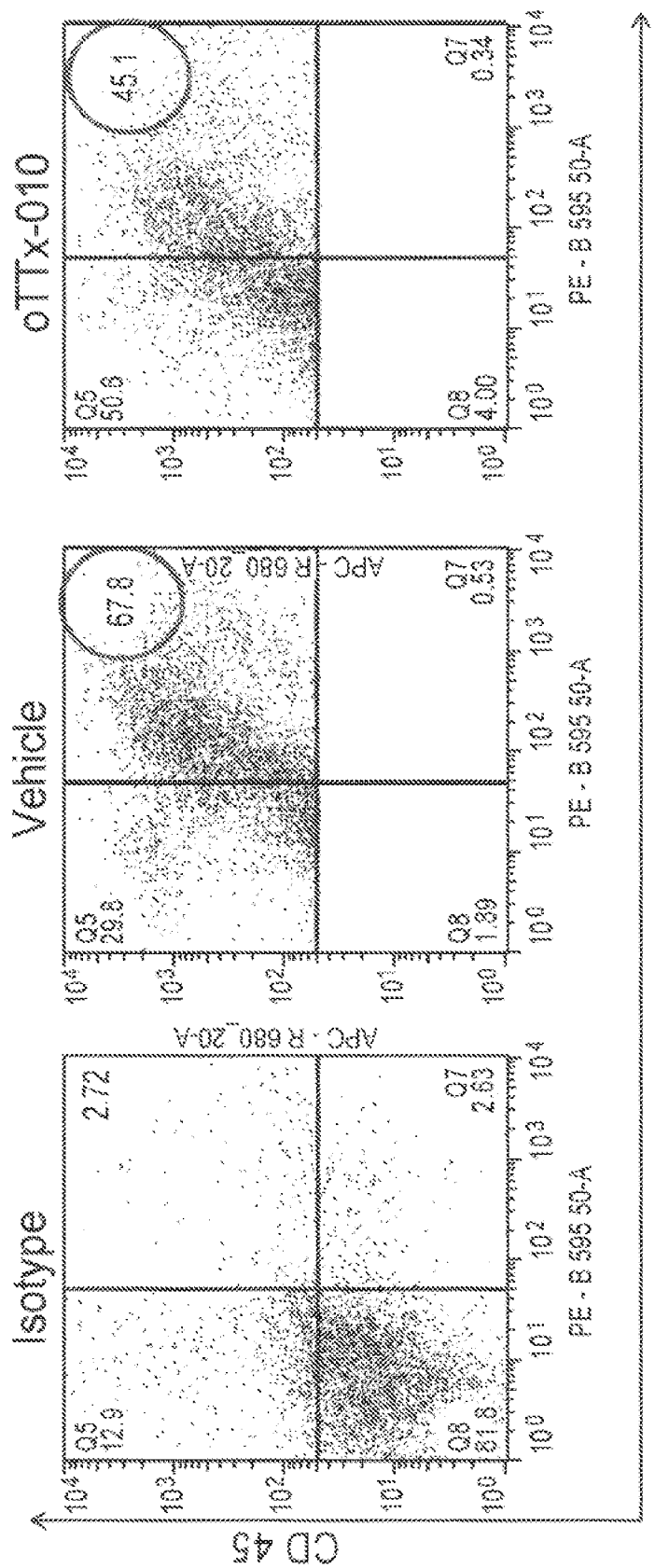
FIG. 13 is a set of flow cytometry graphs showing that percentage of activated immune cells (MHCII+) in the draining lymph node of oTTx-010 treated mice decreased compared to vehicle controls.
Figure 14:
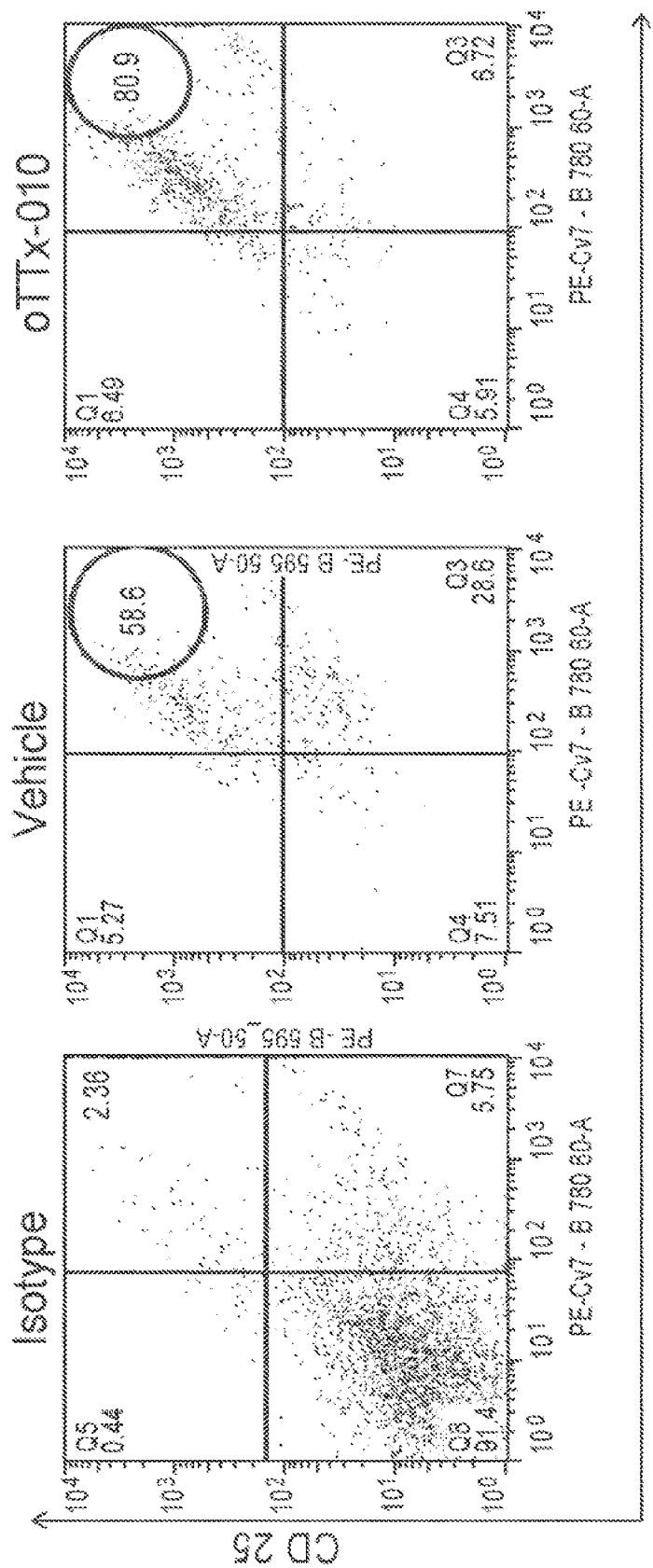
FIG. 14 is a set of flow cytometry graphs showing that T regulatory cells increased in the draining lymph node of oTTx-010 treated mice compared to vehicle (showing more tolerance). Flow cytometry of draining lymph nodes gated on CD45+CD3+ and CD4+ (T cells).

A stabilized form of lipidated chemerin 9 is long acting in a mouse model of neuropathic pain (FIGS. 6A-6B).

Altering the lipid tail of stabilized chemerin 9 alters the pharmacological properties in vitro in part by modifying adherence to the plasma membrane and/or serum albumin binding.

Lipidated chemerin 9 derivatives can be further characterized in a CCI model of neuropathic pain. Lipidated chemerin 9 analogs can be assessed in other mouse models of inflammation, e.g. dust mite model of asthma. Pharmacokinetics profiles of lipidated Chemerin 9 analogs can be compared in vivo. Lipidated peptides can be developed for other targets that modulate inflammation.

TABLE 1

Summary of the potencies of lipidated stable chemerin 9 analogs.
Ligand mediated CMKLR1 canonical Gαi signal transduction varies (potencies assessed +/− wash and +/− albumin).

| Lipid tail | EC50 (no wash0 | EC50 (wash × 3) | EC50 (BSA) (no wash) | EC50 (BSA) (wash × 3) |
|---|---|---|---|---|
| C16 | 2.7 nM | 18.6 nM | 6.4 nM | 520 nM |
| C18:1 | 4.7 nM | 26.4 nM | 12.7 | 2862 nM |
| C18:3 | 45.7 nM | 350 nM | 73.3 nM | ND |
| C10 | 17.8 nM | ND | 17.8 nM | ND |
| C4 | 79.3 nM | ND | 11 nM | ND |
| C16:1 | 12.0 nM | 42.2 | 29.5 | 3143 nM |
| C14:1 | 9.3 nM | 100 nM | 26.2 nM | 1821 nM |
| Cholesterol | 84.5 nm | 445 nM | 108 nM | 13460 nM |
| none | 35.2 nM | ND | 5.1 nM | ND |

TABLE 2

Potencies and efficacies of lipidated stable chemerin analogs.

| Lipid tail | EC50 | Max Efficacy (% 10 µM s-Stable chem9) |
|---|---|---|
| C16 | 3.23 nM | 164.8% |
| C18:1 | 17.4 nM | 159.7% |
| C18:3 | 180.6 nM | 110.1% |
| C10 | 23.12 nM | 98.29% |
| C4 | 223.13 nM | 89.7% |
| C16:1 | 80.84 nM | 153.6% |
| C14:1 | 51.85 nM | 123.6% |
| Cholesterol | 131.2 nM | 149.3% |
| none | 31.92 nM | 100% |
| C16-CKK4-NH$_2$ (nonspecific peptide) | ND | ND |

Example 2

Stable lipidated chemerin was assessed in mouse models of DED and corneal inflammation.

In the DED mouse model, scopolamine is injected 3 times/day to decrease tear production in mice. Fenestrated cages and 4 fans around the cage working 24 hours/day are used to induce desiccating stress and dry eyes. oTTx-010 is administered to the mice to assess treatment efficacy. Vehicle is administered as control. Results show that topical oTTx-010 can be a potential treatment for the DED to decrease clinical symptoms and signs and improve immune tolerance (FIGS. 11-14).

Figure 15:
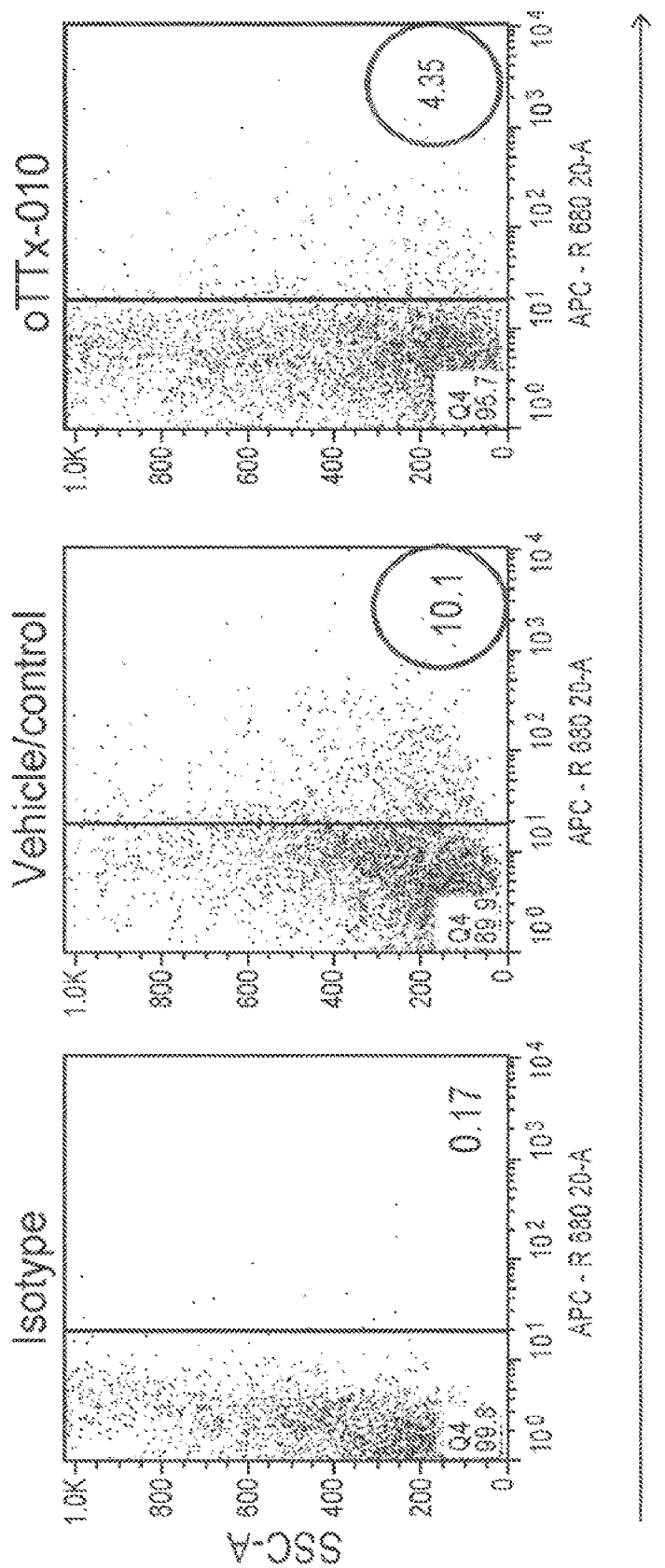
FIG. 15 is a set of flow cytometry graphs showing that cell infiltration decreases after topical application of oTTx-010 compared to vehicle. Flow cytometry of pulled corneas was performed on day 3 post cautery. Mice were treated topically three times a day with 10 µL of oTTx-010 or vehicle for 3 days. 10 µL of 210 nanomolar oTTx-010 in 1×PBS solution=4.2 micrograms oTTx-010/dose.
Figure 2:
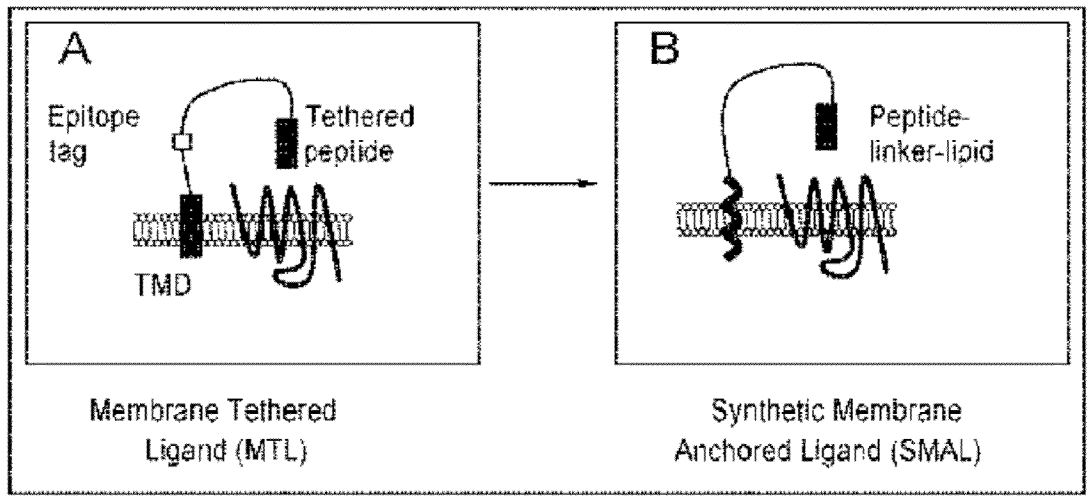

Thermal cautery is a mouse model of corneal inflammation (see Arch Ophthalmol. 2003 Hamrah et al.). Results show that topical oTTx-010 can be applied as a new treatment to decrease inflammation in the eye (FIG. 15).

What is claimed is:

1. A method of reducing irritated or burning eyes in a human subject having dry eye disease, the method comprising topically administering to an eye of the human subject a therapeutically effective amount of a composition, wherein the composition comprises:
   a chemerin fragment consisting of the sequence of Y-F-P-G-Q-F-A-F-S(SEQ ID NO.: 2) or a chemerin analog consisting of the sequence of Y*-F-L-P-S*-Q-F-A*-Tic-S(SEQ ID NO.: 3), wherein * denotes D amino acids and Tic represents 1,2,3,4-tetrahydroisoquinoline-3-carboxylic acid;
   a lipid entity selected from the group consisting of α-linolenic acid, γ-linolenic acid, palmitic acid, vaccenic acid, oleic acid, and elaidic acid; and
   a linker connecting the lipid entity to the chemerin fragment or chemerin analog, wherein the linker comprises polyethylene glycol, KGG, or a combination thereof.

2. The method of claim 1, wherein the composition is administered once a day, twice a day, or thrice a day.

3. The method of claim 1, wherein the lipid entity is linked at or near the N-terminus of the chemerin fragment or chemerin analog.

4. The method of claim 1, wherein a combination of the lipid entity and the linker is palmitate-PEG$_8$KGG.

5. The method of claim 1, wherein the composition is formulated for topical administration as eye drops.

6. A method of reducing irritated or burning eyes in a human subject having dry eye disease, the method comprising topically administering to an eye of the human subject a therapeutically effective amount of a composition, thereby increasing tear film stability, wherein the composition comprises:
   a chemerin fragment consisting of the sequence of Y-F-P-G-Q-F-A-F-S(SEQ ID NO.: 2) or a chemerin analog consisting of the sequence of Y-F-L-P-S-Q-F-A-Tic-S (SEQ ID NO.: 3), wherein Tic represents 1,2,3,4-tetrahydroisoquinoline-3-carboxylic acid;

a lipid entity selected from the group consisting of α-linolenic acid, γ-linolenic acid, palmitic acid, vaccenic acid, oleic acid, and elaidic acid; and a linker connecting the lipid entity to the chemerin fragment or chemerin analog, wherein the linker comprises polyethylene glycol, KGG, or a combination thereof.

7. A method of reducing blurred vision in a human subject having dry eye disease, the method comprising topically administering to an eye of the human subject a therapeutically effective amount of a composition, wherein the composition comprises:

a chemerin fragment consisting of the sequence of Y-F-P-G-Q-F-A-F-S(SEQ ID NO.: 2) or a chemerin analog consisting of the sequence of Y*-F-L-P-S*-Q-F-A*-Tic-S(SEQ ID NO.: 3), wherein * denotes D amino acids and Tic represents 1,2,3,4-tetrahydroisoquinoline-3-carboxylic acid;

a lipid entity selected from the group consisting of α-linolenic acid, γ-linolenic acid, palmitic acid, vaccenic acid, oleic acid, and elaidic acid; and a linker connecting the lipid entity to the chemerin fragment or chemerin analog, wherein the linker comprises polyethylene glycol, KGG, or a combination thereof.

8. A method of reducing blurred vision in a human subject having dry eye disease, the method comprising topically administering to an eye of the human subject a therapeutically effective amount of a composition, wherein the composition comprises:

a chemerin fragment consisting of the sequence of Y-F-P-G-Q-F-A-F-S(SEQ ID NO.: 2) or a chemerin analog consisting of the sequence of Y-F-L-P-S-Q-F-A-Tic-S (SEQ ID NO.: 3), wherein Tic represents 1,2,3,4-tetrahydroisoquinoline-3-carboxylic acid;

a lipid entity selected from the group consisting of α-linolenic acid, γ-linolenic acid, palmitic acid, vaccenic acid, oleic acid, and elaidic acid; and a linker connecting the lipid entity to the chemerin fragment or chemerin analog, wherein the linker comprises polyethylene glycol, KGG, or a combination thereof.

* * * * *

UNITED STATES PATENT AND TRADEMARK OFFICE
CERTIFICATE OF CORRECTION

Page 1 of 3

PATENT NO. : 12,053,501 B2
APPLICATION NO. : 17/521366
DATED : August 6, 2024
INVENTOR(S) : Charles Cohen et al.

It is certified that error appears in the above-identified patent and that said Letters Patent is hereby corrected as shown below:

In the Drawings

Figure 1:

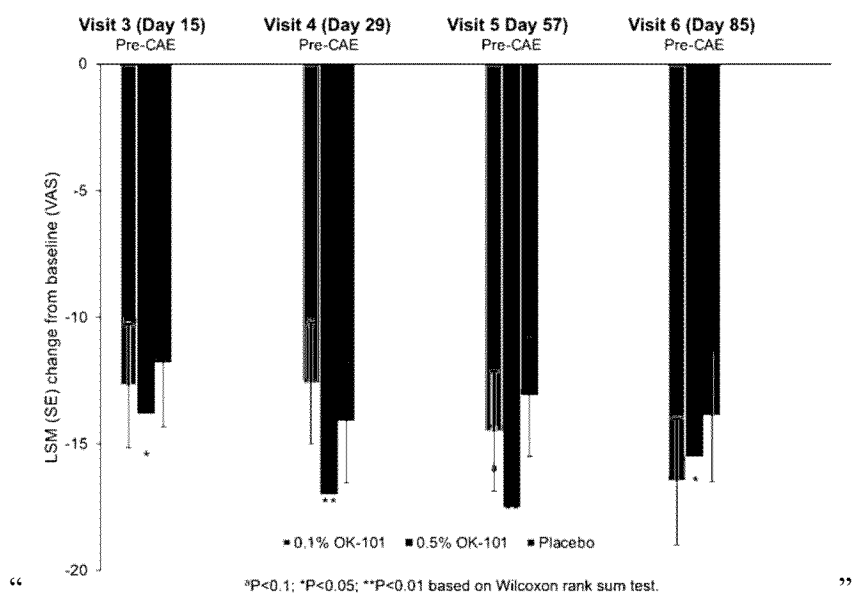

"                                                                                      "

Signed and Sealed this
Eighth Day of October, 2024

Katherine Kelly Vidal
*Director of the United States Patent and Trademark Office*

CERTIFICATE OF CORRECTION (continued)

U.S. Pat. No. 12,053,501 B2

Page 2 of 3

Should read:

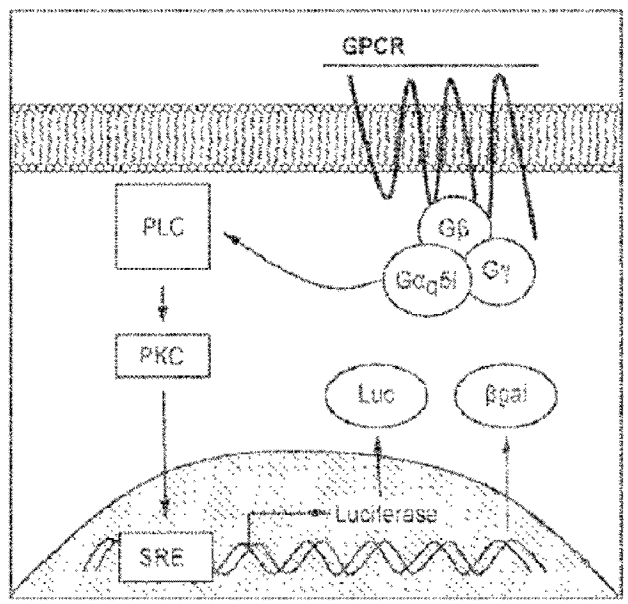

FIG. 1

Figure 2:

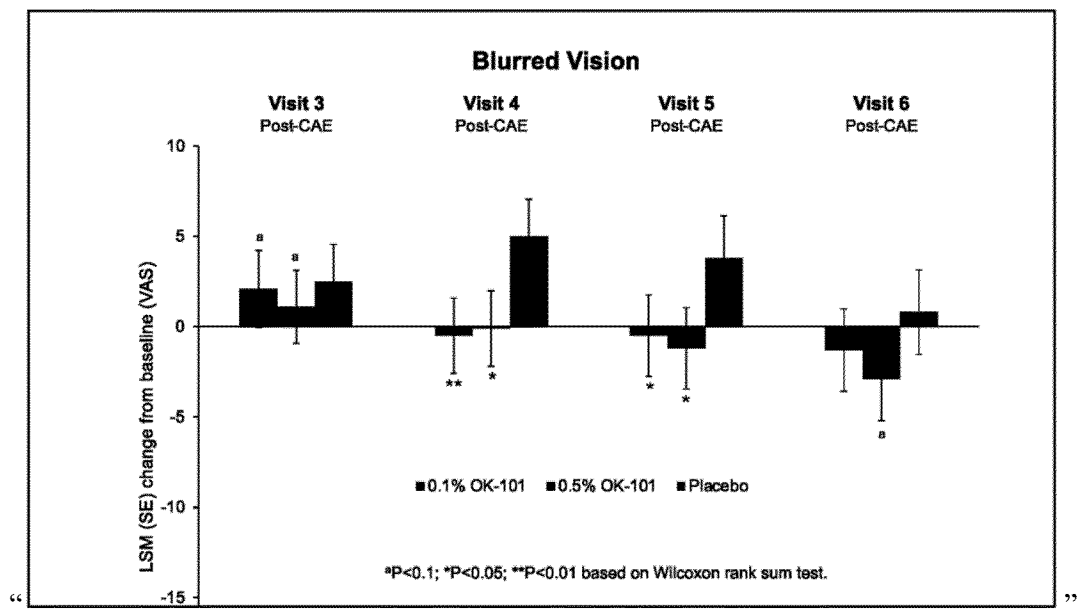

Should read:

SEQUENCE LISTING

```
<160> NUMBER OF SEQ ID NOS: 4

<210> SEQ ID NO 1
<211> LENGTH: 163
<212> TYPE: PRT
<213> ORGANISM: Homo sapiens

<400> SEQUENCE: 1

Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser

<210> SEQ ID NO 2
<211> LENGTH: 9
<212> TYPE: PRT
<213> ORGANISM: Homo sapiens

<400> SEQUENCE: 2

Tyr Phe Pro Gly Gln Phe Ala Phe Ser
1               5

<210> SEQ ID NO 3
<211> LENGTH: 10
<212> TYPE: PRT
<213> ORGANISM: Artificial Sequence
<220> FEATURE:
<223> OTHER INFORMATION: Artificial polypeptide
<220> FEATURE:
<221> NAME/KEY: MOD_RES
<222> LOCATION: (1)..(1)
<223> OTHER INFORMATION: D-Tyr
```

```
<220> FEATURE:
<221> NAME/KEY: MOD_RES
<222> LOCATION: (5)..(5)
<223> OTHER INFORMATION: D-Ser
<220> FEATURE:
<221> NAME/KEY: MOD_RES
<222> LOCATION: (8)..(8)
<223> OTHER INFORMATION: D-Ala
<220> FEATURE:
<221> NAME/KEY: MOD_RES
<222> LOCATION: (9)..(9)
<223> OTHER INFORMATION: 1,2,3,4-tetrahydroisoquinoline-3-carboxylic
      acid

<400> SEQUENCE: 3

Xaa Phe Leu Pro Xaa Gln Phe Xaa Xaa Ser
1               5                   10

<210> SEQ ID NO 4
<211> LENGTH: 137
<212> TYPE: PRT
<213> ORGANISM: Homo sapiens

<400> SEQUENCE: 4

Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
                20                  25                  30

Glu Ser Ala Val Asp Thr Pro Phe Pro Ala Gly Ile Phe Val Arg Leu
            35                  40                  45

Glu Phe Lys Leu Gln Gln Thr Ser Cys Arg Lys Arg Asp Trp Lys Lys
        50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
                85                  90                  95

Cys Pro Ile Glu Thr Gln Val Leu Arg Glu Ala Glu Glu His Gln Glu
            100                 105                 110

Thr Gln Cys Leu Arg Val Gln Arg Ala Gly Glu Asp Pro His Ser Phe
        115                 120                 125

Tyr Phe Pro Gly Gln Phe Ala Phe Ser
    130                 135
```